United States Patent
Dieterle et al.

(10) Patent No.: US 8,642,826 B2
(45) Date of Patent: Feb. 4, 2014

(54) PROCESS FOR LONG-TERM OPERATION OF A CONTINUOUS HETEROGENEOUSLY CATALYZED PARTIAL DEHYDROGENATION OF A HYDROCARBON TO BE DEHYDROGENATED

(75) Inventors: Martin Dieterle, Ludwigshafen (DE); Catharina Klanner, Ludwigshafen (DE); Götz-Peter Schindler, Ludwigshafen (DE); Klaus Joachim Müller-Engel, Stutensee (DE); Jens Scheidel, Hirschberg (DE); Christoph Adami, Weinheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 1565 days.

(21) Appl. No.: 11/829,424

(22) Filed: Jul. 27, 2007

(65) Prior Publication Data

US 2008/0045685 A1    Feb. 21, 2008

Related U.S. Application Data

(60) Provisional application No. 60/833,776, filed on Jul. 28, 2006.

(30) Foreign Application Priority Data

Jul. 28, 2006    (DE) .......................... 10 2006 035 718

(51) Int. Cl.
   *C07C 5/333*    (2006.01)
(52) U.S. Cl.
   USPC ........... 585/659; 585/440; 585/441; 585/443; 585/654; 585/656; 585/658
(58) Field of Classification Search
   USPC ......... 585/654, 659, 660, 440, 441, 443, 656, 585/658; 422/198
   See application file for complete search history.

(56) References Cited

U.S. PATENT DOCUMENTS 2,452,569 A * 11/1948 Houdry .......................... 208/74
3,855,330 A * 12/1974 Mendelsohn et al. ........ 585/441

(Continued)

FOREIGN PATENT DOCUMENTS

DE    199 37 107 A1    2/2001
DE    100 28 582 A1    12/2001

(Continued)

OTHER PUBLICATIONS

Gascón, et al., "Propane Dehydrogenation over a Cr2O3/Al2O3 Catalyst: Transient Kinetic Modeling of Propene and Coke Formation" in Applied Catalysis A: General, 248 (2003), 105-116.*

(Continued)

*Primary Examiner* — In Suk Bullock
*Assistant Examiner* — Bradley Etherton
(74) *Attorney, Agent, or Firm* — Oblon, Spivak, McClelland, Maier & Neustadt, L.L.P.

(57) ABSTRACT

A process for long-term operation of a continuous heterogeneously catalyzed partial dehydrogenation of a hydrocarbon to be dehydrogenated, in which a reaction gas mixture stream comprising the hydrocarbon to be dehydrogenated in a molar starting amount KW is conducted through an overall catalyst bed comprising the total amount M of dehydrogenation catalyst and the deactivation of the overall catalyst bed is counteracted in such a way that, with increasing operating time, the contribution to the conversion in the first third of the total amount M of dehydrogenation catalyst in flow direction decreases, the contribution to the conversion in the last third of the total amount M of dehydrogenation catalyst in flow direction increases, and the contribution to the conversion in the second third of the total amount M of dehydrogenation catalyst in flow direction passes through a maximum.

34 Claims, 3 Drawing Sheets

(56) References Cited

U.S. PATENT DOCUMENTS

| | | | |
|---|---|---|---|
| 4,788,371 A | 11/1988 | Imai et al. | |
| 4,886,928 A | 12/1989 | Imai et al. | |
| 5,235,121 A | 8/1993 | Brinkmeyer et al. | |
| 5,430,209 A | 7/1995 | Agaskar et al. | |
| 5,491,275 A * | 2/1996 | Vora et al. | 585/659 |
| 5,510,557 A * | 4/1996 | Gartside et al. | 585/654 |
| 5,527,979 A | 6/1996 | Agaskar et al. | |
| 5,530,171 A | 6/1996 | Agaskar et al. | |
| 5,563,314 A | 10/1996 | Agaskar et al. | |
| 5,689,029 A * | 11/1997 | Vora et al. | 585/659 |
| 5,994,606 A * | 11/1999 | Iwakura et al. | 585/660 |
| 6,433,222 B1 * | 8/2002 | Eck et al. | 562/600 |
| 6,670,303 B1 | 12/2003 | Heineke et al. | |
| 6,740,228 B1 * | 5/2004 | Verduijn et al. | 208/138 |
| 6,781,017 B2 * | 8/2004 | Machhammer et al. | 568/470 |
| 7,291,761 B2 | 11/2007 | Machhammer et al. | |
| 7,388,109 B2 | 6/2008 | Machhammer et al. | |
| 2006/0004226 A1 | 1/2006 | Machhammer et al. | |
| 2006/0004227 A1 | 1/2006 | Dieterle et al. | |
| 2006/0004229 A1 | 1/2006 | Dieterle et al. | |
| 2006/0122448 A1 * | 6/2006 | Thiagarajan et al. | 585/659 |
| 2006/0258529 A1 | 11/2006 | Diefenbacher et al. | |
| 2007/0088092 A1 | 4/2007 | Klammer et al. | |
| 2007/0099299 A1 | 5/2007 | Simon et al. | |
| 2007/0117998 A1 | 5/2007 | Machhanner et al. | |
| 2007/0123732 A1 | 5/2007 | Dieterle et al. | |
| 2007/0142689 A1 | 6/2007 | Hechler et al. | |
| 2007/0276157 A1 | 11/2007 | Machhammer et al. | |
| 2007/0299278 A1 | 12/2007 | Hechler et al. | |

FOREIGN PATENT DOCUMENTS

| | | | |
|---|---|---|---|
| DE | 102 11 275 A1 | 9/2003 | |
| DE | 10 2004 032 129 A1 | 3/2005 | |
| DE | 10 2004 054 657 A1 | 5/2006 | |
| DE | 10 2005 009 885 A1 | 9/2006 | |
| DE | 10 2005 010 111 A1 | 9/2006 | |
| DE | 10 2005 013 039 A1 | 9/2006 | |
| DE | 10 2005 022 798 A1 | 11/2006 | |
| DE | 10 2005 044 916 A1 | 3/2007 | |
| DE | 10 2005 052 923 A | 5/2007 | |
| DE | 10 2005 057 197 A | 6/2007 | |
| DE | 10 2005 061 626 A1 | 6/2007 | |
| DE | 10 2005 052 917 A1 | 10/2007 | |
| DE | 10 2006 024 901 A1 | 11/2007 | |
| DE | 10 2006 029 790 A1 | 1/2008 | |
| EP | 0 336 622 A2 | 10/1989 | |
| WO | WO 95/23123 | 8/1995 | |
| WO | WO 01/96270 A2 | 12/2001 | |
| WO | WO 01/97961 A1 | 12/2001 | |
| WO | WO 03/076370 A1 | 9/2003 | |
| WO | WO 2004/039755 A2 | 5/2004 | |
| WO | WO 2004/039920 A2 | 5/2004 | |
| WO | WO 2004039920 A2 * | 5/2004 | C10G 11/02 |
| WO | WO 2006/002713 A1 | 1/2006 | |
| WO | WO 2006/050957 A1 | 5/2006 | |

OTHER PUBLICATIONS

Buchholz, "Polyacrylamides and Poly(Acrylic Acid)" in Ullmann's Encyclopedia of Industrial Chemistry, Wiley-VCH, 2002, available on-line Jun. 15, 2000.*

Ohara, et al "Acrylic Acid and Derivatives" in Ullmann's Encyclopedia of Industrial Chemistry, Wiley-VCH, 2002, available on-line Mar. 15, 2003.*

Penzel, "Polyacrylates" in Ullmann's Encyclopedia of Industrial Chemistry, Wiley-VCH, 2002, available on-line Jun. 15, 2000.*

Dumez, et al., "Dehydrogenation of 1-Butene into Butadiene. Kinetics, Catalyst Coking, and Reactor Design" in Ind. Eng. Chem., Process Des. Dev., 15(2), 291-301 (1976)—month unknown.*

\* cited by examiner

PROCESS FOR LONG-TERM OPERATION OF A CONTINUOUS HETEROGENEOUSLY CATALYZED PARTIAL DEHYDROGENATION OF A HYDROCARBON TO BE DEHYDROGENATED

Figure 1:
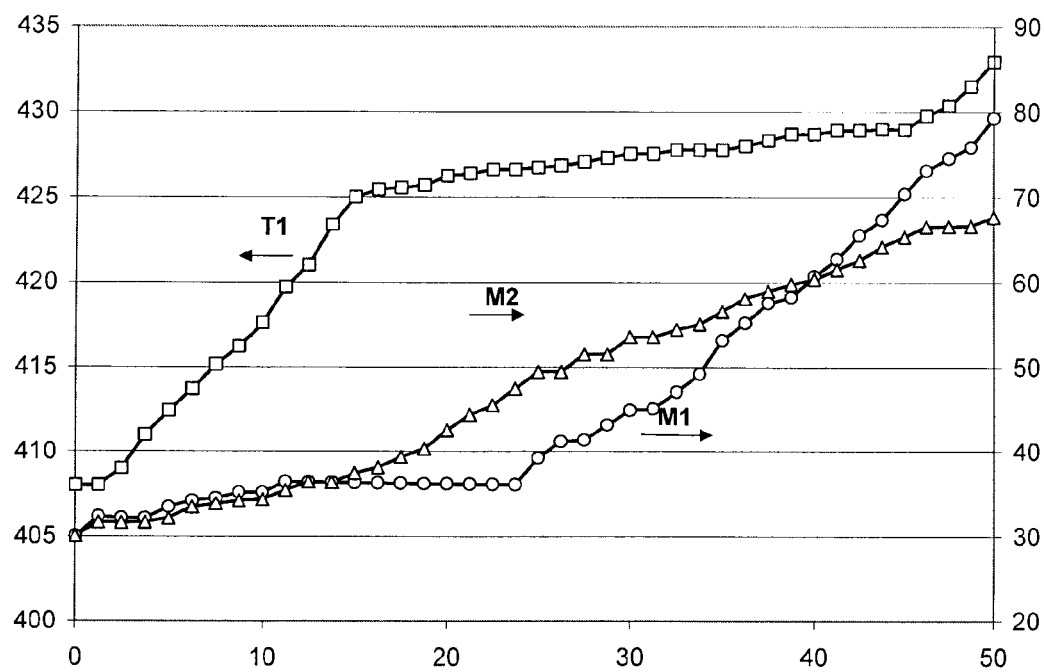
FIG. 1: The counteract deactivation of the overall fixed catalyst bed

The term "dehydrogenated hydrocarbon" used in this application is intended to comprise hydrocarbons whose molecules comprise at least two ("two" are preferred from a performance point of view) hydrogen atoms fewer than the molecules of a hydrocarbon to be dehydrogenated. Otherwise, the term hydrocarbon is intended to comprise substances whose molecules are formed only from the elements carbon and hydrogen.

Hence, dehydrogenated hydrocarbons comprise especially acyclic (linear and/or branched) and cyclic aliphatic hydrocarbons having one or more C,C double bonds in the molecule.

Examples of such aliphatic dehydrogenated hydrocarbons are propene, isobutene, ethylene, 1-butene, 2-butene and butadiene. In other words, the dehydrogenated hydrocarbons include in particular the monounsaturated linear hydrocarbons (n-alkenes) or branched aliphatic hydrocarbons (e.g. isoalkenes), and also the cycloalkenes. Moreover, the dehydrogenated hydrocarbons are also intended to comprise the alkapolyenes (e.g. dienes and trienes) which comprise more than one carbon-carbon double bond in the molecule. However, dehydrogenated hydrocarbons are also intended to comprise hydrocarbon compounds which are obtainable starting from alkylaromatics such as ethylbenzene or isopropylbenzene by dehydrogenation of the alkyl substituents. These are, for example, compounds such as styrene or α-methylstyrene.

Dehydrogenated hydrocarbons are quite generally valuable starting compounds for the synthesis of, for example, functionalized, free-radically polymerizable compounds (e.g. acrylic acid from propene or methacrylic acid from isobutene) and polymerization products thereof. For example, such functionalized compounds can be obtained by partial oxidation of dehydrogenated hydrocarbons. However, dehydrogenated hydrocarbons are also suitable for preparing compounds such as methyl tert-butyl ether (subsequent product of isobutene, which is suitable, for example, as a fuel additive for increasing the octane number). Dehydrogenated hydrocarbons may also be used as such for polymerization themselves.

Useful hydrocarbons to be dehydrogenated in this document are especially the acyclic (linear and/or branched) and cyclic alkanes, but also olefins (whose C,C double bond number is to be increased) (as an example, mention should be made of the heterogeneously catalyzed partial dehydrogenation of n-butenes to butadiene).

In other words, the term "hydrocarbons to be dehydrogenated" in this document comprises, for example, hydrocarbons of the stoichiometry $C_nH_{2n+2}$ where n>1 to n≤20, and of the stoichiometry $C_nH_{2n}$ where n>1 to n≤20, and of the stoichiometry $C_nH_{2n-2}$ where n>2 to n≤20, and n=an integer, especially $C_2$- to $C_{16}$-alkanes, for example ethane (to ethylene), propane (to propylene), n-butane, isobutane (to isobutene), n-pentane, isopentane, n-hexane, n-heptane, n-octane, n-nonane, n-decane, n-undecane, n-dodecane, n-tridecane, n-tetradecane, n-pentadecane and n-hexadecane.

In particular, however, all statements made in this document apply to $C_2$- to $C_6$-alkanes as hydrocarbons to be dehydrogenated and very particularly to $C_2$ to $C_4$ hydrocarbons (especially alkanes, and among these propane in particular). In other words, hydrocarbons to be dehydrogenated in this document are in particular ethane, propane, n-butane and isobutane, but also 1-butene and 2-butene.

In this document, a heterogeneously catalyzed partial dehydrogenation of a hydrocarbon shall be understood to mean a (conventional) dehydrogenation in which free molecular hydrogen is formed at least as an intermediate and the dehydrogenation step accordingly proceeds endothermically (as a subsequent step, an exothermic hydrogen combustion may be included). In contrast, in a heterogeneously catalyzed partial oxydehydrogenation of the hydrogen pulled from the hydrocarbon to be dehydrogenated by oxygen present is pulled out directly as water ($H_2O$). The dehydrogenation step of a heterogeneously catalyzed partial oxydehydrogenation therefore in principle proceeds exothermically.

Typically, a (conventional) heterogeneously catalyzed partial dehydrogenation (for example as described at the outset of this document) of a hydrocarbon to be dehydrogenated (for example propane) requires comparatively high reaction temperatures. Typical reaction temperatures are from 300 to 850° C. or to 800° C., or from 400 to 700° C.

The conversion achieved is normally not limited kinetically but rather by the thermodynamic equilibrium.

As a markedly endothermic reaction in which one molecule of hydrogen is additionally obtained per molecule of, for example, propane to be dehydrogenated to propylene, high temperatures and removal of the $H_2$ reaction product shift the equilibrium position toward the dehydrogenated hydrocarbon as the desired target product, as does lowering the partial pressure by inert dilution. In this document, an inert gas (inert diluent gas) shall generally be understood to mean a reaction gas mixture constituent which essentially behaves chemically inertly under the conditions of the appropriate reaction and—each inert reaction gas mixture constituent taken alone—remains chemically unchanged to an extent of more than 95 mol %, preferably to an extent of more than 97 mol % or to an extent of more than 99 mol %. Examples of typical inert diluent gases are, for example, $N_2$, $CO_2$, $H_2O$, noble gases such as He, Ne and Ar, and mixtures of these gases, etc.

Since the dehydrogenation step to the dehydrogenated hydrocarbon in a heterogeneously catalyzed partial dehydrogenation of a hydrocarbon to be dehydrogenated (e.g. propane) proceeds endothermically, the heat of reaction required for the desired dehydrogenation conversion has to be supplied to the reaction gas either before the heterogeneously catalyzed dehydrogenation and/or in the course of the heterogeneously catalyzed dehydrogenation.

In the simplest manner, a heterogeneously catalyzed partial dehydrogenation can therefore be performed as follows in an adiabatic (overall) catalyst bed.

The reaction mixture comprising the hydrocarbon to be dehydrogenated is heated to its start temperature (typically from 300 to 850° C., frequently from 400 to 800° C., in many cases from 450 to 750° C., or from 500 to 700° C., or from 550 to 650° C.), and then conducted through the (overall) catalyst bed in an adiabatic pass (thermally insulated from the environment). Depending on the conversion and inert dilution selected, the reaction gas mixture will cool by from about 30 to 200° C. as it passes through the (overall) catalyst bed.

When the overall catalyst bed which, in total, comprises the amount M of a dehydrogenation catalyst is divided (theoretically) into three successive sections in flow direction of the reaction gas mixture, of which each comprises one third of the total amount M of the dehydrogenation catalyst, at the start (i.e. when the fresh or freshly regenerated overall catalyst bed is put into operation) of the heterogeneously catalyzed partial dehydrogenation just described, a proportion of A mol % of the molar starting amount KW is converted in (single) pass of the reaction gas mixture stream (which comprises the molar starting amount KW of the hydrocarbon to be dehydrogenated) through the first third of the amount M in flow direction, a proportion of B mol % of the starting amount KW is converted in (single) pass of the reaction gas mixture stream through the second third of the amount M in flow direction, and a proportion of C mol % of the molar starting amount KW of the hydrocarbon to be dehydrogenated is converted to dehydrogenated hydrocarbon in (single) pass of the reaction gas mixture stream through the last third of the amount M in flow direction, where normally, of course, A>B>C.

Overall, in (single) pass of the reaction gas mixture stream through the overall catalyst bed, G=(A+B+C) mol % of the molar starting amount KW of hydrocarbon to be dehydrogenated present therein is dehydrogenated to dehydrogenated hydrocarbon (based on single pass).

The (overall) catalyst bed may be (as is quite generally the case in processes according to the invention) at least one fixed catalyst bed, at least one fluidized catalyst bed, at least one moving catalyst bed or a combination (for example a series arrangement) of more than one of the aforementioned catalyst bed variants. Preferably in accordance with the invention, the (overall) catalyst bed is generally at least one fixed catalyst bed, which is why all statements made in this document are valid especially in this regard.

In other words, in the simplest manner, in the above-described adiabatic operating mode, the at least one fixed catalyst bed (the overall fixed catalyst bed) may be disposed in an adiabatic shaft reactor (designed so as to be thermally insulated form its environment). A shaft reactor is obtained by a material shell which is in contact with the reaction chamber and has at least one first orifice for supplying a reaction gas mixture comprising the hydrocarbon to be dehydrogenated into the reaction chamber and at least one second orifice for withdrawing a product gas stream from the reaction chamber. In the shaft (reaction chamber) with an externally adiabatic (thermally insulated) configuration is preferably disposed at least one fixed catalyst bed which is flowed through by the reaction gas mixture. During the residence time in the at least one fixed catalyst bed, the desired partial dehydrogenation of the hydrocarbon to be dehydrogenated (e.g. propane) to the dehydrogenated hydrocarbon proceeds. Normally, the at least one fixed catalyst bed present in the adiabatic shaft furnace reactor will be only a continuous fixed catalyst bed, and the temperature of the reaction gas mixture comprising the hydrocarbon to be dehydrogenated will decrease gradually in flow direction over the length of this fixed catalyst bed, which of course restricts the resulting conversion.

Increasing start temperature of the reaction gas mixture is normally accompanied by increasing dehydrogenation conversions G in the aforementioned operating mode, but increased start temperatures promote the thermal cracking undesired as a side reaction to a comparatively high degree (dehydrogenation (cleavage of C—H) is frequently naturally kinetically disfavored compared to cracking (cleavage of C—C); a reversal of these conditions requires the presence of catalyst which selectively promotes the dehydrogenation and is the basis of heterogeneously catalyzed dehydrogenations of hydrocarbons to be dehydrogenated).

In the above context, additional use of steam as an inert diluent gas in the reaction gas mixture is therefore advantageous for a heterogeneously catalyzed partial dehydrogenation and is in practice essentially always done. This is because steam has an increased molar heat capacity in comparison to other possible diluent gases, which reduces the temperature decrease discussed above and promotes increased values for G in the case of the aforementioned additional use.

However, with increasing steam content of the reaction gas mixture, the volume of the reaction gas mixture firstly grows (which causes increased capital costs), and an increased steam content secondly promotes, as a further undesired side reaction, the steam reformation of the hydrocarbons, in which the latter react with steam to give CO, $CO_2$ and $H_2$. The amount of steam which can be used additionally in the individual case with a still negligible degree of undesired steam reformation is dependent primarily upon the absolute pressure (this will generally be from 0.2 to 10 bar or form 0.5 to 6 or to 3 bar) at which the heterogeneously catalyzed dehydrogenation is performed, and upon the dehydrogenation catalyst used.

In principle, the temperature decrease which restricts the dehydrogenation conversion G can additionally be counteracted by external temperature control. In this document, external temperature control shall generally be understood to mean temperature control by indirect heat exchange. Such external temperature control is possible in a simple manner in a heterogeneously catalyzed dehydrogenation of a hydrocarbon, for example, by externally heating the reactor comprising the (overall) catalyst bed and hence the (overall) catalyst bed itself. Such a procedure is described by way of example in U.S. Pat. No. 5,235,121.

Alternatively, it is also possible in principle to adhere to the principle of the adiabatic operating mode of the overall catalyst bed and to distribute it, for example, over a plurality of catalyst bed stages arranged in succession or over a plurality of dehydrogenation reactors arranged in succession, and to subject the reaction gas mixture beyond each adiabatic partial catalyst bed to heating by indirect heat exchange, i.e. by external temperature control.

In other words, in a particularly advantageous manner, a heterogeneously catalyzed hydrocarbon (e.g. propane) dehydrogenation can be operated in an externally adiabatic shaft reactor when it is designed as a staged reactor.

A staged reactor comprises, in spatial succession, for example, more than one (partial) fixed catalyst bed which catalyzes the dehydrogenation in the shaft (enclosed reaction chamber). The number of (partial) fixed catalyst beds may, for example, be from 1 to 20, appropriately from 2 to 8, or from 3 to 6. In general, the (partial) fixed catalyst beds are arranged in radial or else in axial succession.

In a manner which is particularly simple to realize, the (partial) fixed catalyst beds are arranged in axial succession in the externally adiabatic shaft along its axis pointing in flow direction of the reaction gas mixture stream. They may, though, be arranged in the annular gaps of concentric grids in the shaft. It is also possible to arrange the annular gap in segments one on top of another in the shaft and to conduct the reaction gas, after radial passage in one segment, into the next segment above it or below it.

On its way from one (partial) fixed catalyst bed to the next (partial) fixed catalyst bed, the reaction gas mixture can then, for example, be subjected to indirect intermediate heating (externally controlled temperature profile) by passing it over and/or through indirect heat exchangers (for example heat exchanger ribs, or heat exchanger plates, or heat exchanger tube bundles) which are operated by means of hot gases and/or liquids and are mounted between the fixed bed stages in the otherwise adiabatic shaft.

In a shaft furnace staged reactor equipped in such a way, it is generally sufficient for dehydrogenation conversions G (e.g. propane propylene conversions) based on single pass of the reaction gas, especially with additional use of steam as an inert diluent gas, of up to 50 mol %, frequently up to 40 mol % (for example when the catalysts described in DE-A 10 2005 044 9216 and in DE-A 199 37 107 are used, especially those listed by way of example), to conduct the reaction gas mixture comprising the hydrocarbon to be dehydrogenated, preheated to a temperature of from 350 or 400 or 450 to 550° C. (preferably from 400 to 500° C.) into the shaft (the enclosed, externally adiabatic reaction chamber accommodating the (partial) fixed catalyst beds) and, within the shaft, within the staged reaction chamber, to keep it at least within this temperature range by indirect heat exchange (externally controlled temperature profile). The initial pressure of the reaction gas mixture input stream, on entry thereof into the first (partial) fixed catalyst bed in flow direction, appropriately from an application point of view, will be from >1 to 10 bar, advantageously from 1.5 to 5 bar. In principle, this inlet pressure may also be less than 1 bar. For example, it may also be from 0.2 to <1 bar.

However, it is even simpler from an application point of view to perform the intermediate heating outlined above in a direct way (internally controlled temperature profile). To this end, a gas comprising molecular oxygen can be added in each case to the reaction gas mixture (to the reaction gas) between two (partial) fixed catalyst beds on its way from (partial) fixed catalyst bed to (partial) fixed catalyst bed to a restricted extent, which in each case generates a reaction gas mixture stream comprising molecular oxygen, molecular hydrogen and hydrocarbon, and typically steam.

When the next (partial) fixed catalyst bed in flow direction of this reaction gas mixture stream is configured by suitable selection of the active composition in such a way that the dehydrogenation catalyst also catalyzes the combustion reaction of molecular hydrogen with molecular oxygen to give water and/or the combustion reaction of hydrocarbon present in the reaction gas mixture stream to carbon oxides and water, or catalysts which selectively catalyze these combustions are added to the (partial) fixed catalyst bed in addition to the dehydrogenation catalyst, restricted exothermic combustion of molecular hydrogen present in the reaction gas mixture and/or of hydrocarbon present in the reaction gas mixture with molecular oxygen (to $H_2O$ and to $H_2O$ and carbon oxides respectively) will proceed, if appropriate, before and/or superimposed on the heterogeneously catalyzed dehydrogenation as the reaction gas mixture passes through this (partial) fixed catalyst bed. The heat of reaction released can then be consumed in the subsequent and/or simultaneous dehydrogenation of endothermic character. The resulting combustion products, such as $CO_2$, $H_2O$ and the $N_2$ which accompanies the molecular oxygen required for the combustion if appropriate (if the oxygen source used is, for example, air), are inert diluent gases advantageous for the heterogeneously catalyzed dehydrogenation. The weighting between "hydrogen combustion" and "hydrocarbon combustion" can be influenced primarily by the catalyst selection. Useful catalysts which catalyze the combustion of molecular hydrogen and/or hydrocarbon comparatively selectively include, for example, those of the documents U.S. Pat. No. 4,788,371, U.S. Pat. No. 4,886,928, U.S. Pat. No. 5,430,209, U.S. Pat. No. 5,530,171, U.S. Pat. No. 5,527,979 and U.S. Pat. No. 5,563,314.

Dominant "hydrogen combustion" is typically preferred over dominant "hydrocarbon combustion", since it causes both increased selectivity of formation of the dehydrogenated hydrocarbon compound and increased dehydrogenation conversion based on single pass of the reaction gas mixture through the staged reactor. It generally exists when the (partial) fixed catalyst bed flowed through in each case comprises only dehydrogenation catalyst (especially those recommended in DE-A 199 37 107 (especially the catalysts detailed by way of example in this DE-A)), since they are generally capable of catalyzing not only the dehydrogenation of the hydrocarbon to be dehydrogenated (e.g. propane), but also the combustion of molecular hydrogen and of hydrocarbons. The hydrogen combustion proceeds generally very much faster both in comparison to the dehydrogenation of the hydrocarbon to be dehydrogenated (e.g. propane) and in comparison to, for example, its combustion in the case of a competition situation over these catalysts (i.e. they generally require the lowest activation energy under the given conditions for the combustion of molecular hydrogen).

Depending on the extent of the combustion reaction performed (i.e. also depending upon the amount of molecular oxygen supplied), the overall reaction profile in single pass of the reaction gas mixture through the staged reactor may be configured so as to be endothermic (negative), or autothermal (essentially zero) or exothermic (positive) with regard to the integral thermal character (i.e. with regard to the gross thermal character).

The combustion of molecular hydrogen affords about twice that amount of thermal energy which is consumed for the formation of the same amount of hydrogen in the course of the dehydrogenation.

It will be appreciated that it is also possible, between two (partial) catalyst beds, to make use either of the principle of internal temperature control or of the principle of external temperature control. Moreover, the isothermicity of a heterogeneously catalyzed partial dehydrogenation of a hydrocarbon can also additionally be improved by, in the staged reaction chamber between (and/or within) the (partial) fixed catalyst beds, introducing closed internals (for example tubular) which have favorably but not necessarily been evacuated before their filling. Such internals may, as already stated, also be placed into the particular (partial) fixed catalyst bed. These internals comprise suitable solids or liquids which evaporate or melt above a certain temperature and consume heat as they do so, and, where the temperature goes below this temperature, condense again and release heat as they do so. In principle, it is additionally possible to conduct fluid (gaseous and/or liquid) heat carriers outside the material shells of the shaft reactor, in order to further improve the isothermicity. However, the application complexity is considerable, which is why preference is generally given to the externally adiabatic configuration.

The measure of internal temperature control described is also employed willingly in order to heat the reaction gas mixture supplied to the first catalyst bed in flow direction of the reaction gas mixture to the desired reaction temperature. For this purpose, an appropriate amount of molecular oxygen is added actually to the reaction gas mixture which comprises the hydrocarbon to be hydrogenated and is conducted into the shaft reactor. In addition, molecular hydrogen may be added to this reaction gas mixture before it enters the first (fixed) catalyst bed for the purpose of such a heating combustion. However, it is also possible to dispense with such a hydrogen addition. The internal temperature control for the purpose of heating the reaction mixture to reaction temperature is then effected essentially only by hydrogen combustion. It is also possible to supply heat to the reaction gas mixture between the (partial) catalyst beds by supplying superheated steam to the reaction gas. In many cases, the reaction gas mixture supplied to the first (fixed) partial catalyst bed is also brought to reaction temperature in another way. For example, the starting gas streams from which the reaction gas mixture supplied to the first (fixed) catalyst bed is constituted may already have appropriate temperatures. These starting gas streams may also already comprise molecular oxygen, so that the problem of metered addition of a gas comprising molecular oxygen to a reaction gas mixture flowing toward the first (fixed) catalyst bed in flow direction in the shaft does not occur, or the reaction gas mixture which is to be conducted through the dehydrogenation reactor and to be heated is conducted in indirect heat exchange to the hot product gas mixture conducted out of the dehydrogenation reactor.

In principle, the above-described variants of a heterogeneously catalyzed partial dehydrogenation of a hydrocarbon to be dehydrogenated to a dehydrogenated hydrocarbon are known (cf., for example, DE-A 10 2005 061 626, DE-A 10 2005 057 197, DE-A 10 2005 052 923, DE-A 10 2005 052 917, DE-A 10 2005 022 798, DE-A 10 2005 009 885, DE-A 10 2005 010 111, DE-A 10 2004 032 129, DE-A 10 2005 013 039, WO 03/076370, DE-A 102 11 275, WO 01/96270, WO 2004/039920, DE-A 10 2004 054 657, WO 2006/050957, DE-A 10 2006 029 790, DE-A 10 2006 024 901 and the prior art cited in these documents).

Irrespective of how the heterogeneously catalyzed partial dehydrogenation is configured in the specific case and what kind of temperature control is employed, what is common to all of the variants described is that, when they are put into operation (i.e. over the fresh or freshly regenerated overall catalyst bed), for the (theoretical) (partial) catalyst beds, the dehydrogenation conversion relation A>B>C is generally still satisfied, and none of them succeeds in entirely suppressing the thermal cracking of the hydrocarbons undesired as a side reaction. In other words, undesired by-products formed in all cases are small amounts of high-boiling high molecular weight organic compounds (thermal decomposition products), up to and including elemental carbon, which are deposited on the catalyst surface and thus increasingly deactivated with increasing operating time. Steam used additionally as an inert diluent gas in the reaction gas mixture is capable partly of eliminating carbon deposited on the catalyst surface again by the principle of coal gasification, but not of completely preventing it. Similarly, molecular hydrogen already used (added) in the reaction gas mixture supplied to the first (partial) fixed catalyst bed (or other (partial) catalyst bed) regularly prolongs the lifetime of the dehydrogenation catalysts, but is likewise incapable of preventing its gradual deactivation.

Such a deactivation is disadvantageous in that increasing catalyst deactivation under otherwise unchanged dehydrogenation conditions is accompanied by an increasing decline in the conversion, based on single pass of the reaction gas mixture through the overall catalyst bed, of hydrocarbon to be dehydrogenated to dehydrogenated hydrocarbon, which reduces the space-time yield of dehydrogenated hydrocarbon.

This is disadvantageous especially when the process for heterogeneously catalyzed partial dehydrogenation of the hydrocarbon to be dehydrogenated is followed immediately, for example, by a process for the heterogeneously catalyzed partial oxidation of dehydrogenated hydrocarbon obtained (e.g. propylene to acrolein and/or acrylic acid), preferably accompanied by unconverted hydrocarbon to be dehydrogenated (e.g. propane) as an inert gas in the partial oxidation, given that a decreasing space-time yield of dehydrogenated hydrocarbon simultaneously reduces the space-time yield of partial oxidation product in such a case.

What are being sought are therefore processes for heterogeneously catalyzed partial dehydrogenation in which the above-described deactivation of the overall catalyst bed is counteracted in a very elegant manner.

DE-A 10 2005 013 039 gives a prior description of a process for heterogeneously catalyzed partial dehydrogenation in which the overall catalyst bed is divided in the form of three partial catalyst beds between three successive adiabatic reactors (these three reactors together form a reaction zone RZ) (one partial catalyst bed per reactor). Before the reaction gas mixture enters the particular partial catalyst bed, it can be heated to the desired entrance temperature (into the partial catalyst bed) by indirect heat exchange in a preheating zone.

In addition, air is metered to the reaction gas mixture before it enters the particular partial catalyst bed. The reaction gas mixture which enters the first partial catalyst bed in flow direction likewise already comprises added molecular oxygen. The dehydrogenation catalyst used simultaneously catalyzes the combustion of molecular hydrogen and of hydrocarbon. When the fresh or freshly regenerated overall catalyst bed is put into operation, the relation A>B>C is satisfied.

In order to counteract the deactivation of the overall catalyst bed described in DE-A 10 2005 013 039, DE-A 10 2005 013 039 merely comprises the recommendation to change the particular temperature setting of the reaction gas mixture such that the dehydrogenation conversion G based on single pass of the reaction gas mixture through the overall catalyst bed and the resulting space-time yield of dehydrogenated hydrocarbon remain essentially constant.

However, what is disadvantageous about this recommendation is that, with increasing increase in the particular temperature of the reaction gas mixture while retaining the relation A>B>C, the catalyst deactivation can be counteracted but the cause of deactivation is simultaneously intensified with increasing dehydrogenation temperature. In such a procedure, the operating point at which the space-time yield can no longer be maintained even with further increase in the particular temperature of the reaction gas mixture is already reached after a comparatively short operating time.

At this stage at the latest, the dehydrogenation has to be interrupted and the overall catalyst bed regenerated. Such regeneration measures generally consist in (cf. DE-A 100 28 582) flowing an oxygen-comprising gas through the overall catalyst bed at elevated temperature, in order thus to effectively burn off the carbon deposited on the catalyst surface. A subsequent reductive treatment with molecular hydrogen normally concludes the catalyst regeneration.

What is problematic in this context is that the catalyst deactivation regularly comprises a reversible part and an irreversible part.

Another disadvantage of the teaching of DE-A 10 2005 013 039 is that, when the method recommended there by which the catalyst deactivation is to be counteracted before the catalyst regeneration is employed, the aforementioned irreversible part becomes noticeable comparatively rapidly. Presumably to avoid this situation, in WO 01/96008, a catalyst deactivation is not counteracted at all before a regeneration. Against this background, it was an object of the present invention to provide a process for the long-term operation of a heterogeneously catalyzed partial dehydrogenation as described at the outset, in which the deactivation of the overall dehydrogenation catalyst bed is counteracted in a manner which is accompanied by the aforementioned disadvantages only to a lesser extent.

Accordingly, a process has been found for the long-term operation of a continuous heterogeneously catalyzed partial dehydrogenation of a hydrocarbon to be dehydrogenated to a dehydrogenated hydrocarbon, in which, for the purpose of the heterogeneously catalyzed partial dehydrogenation of the hydrocarbon to be dehydrogenated, a reaction gas mixture stream comprising it in a molar starting amount KW is conducted at elevated temperature through an overall catalyst bed which is disposed in a reaction zone RZ and may consist of a plurality of partial catalyst beds arranged in succession in flow direction of the reaction gas mixture stream and comprises in total the amount M (mass) of a dehydrogenation catalyst, in such a way that, at the operating time $t=t_0$, a proportion of A mol % of the molar starting amount KW is converted in (single) pass of the reaction gas mixture stream through the first third of the amount M in flow direction, a proportion of B mol % of the molar starting amount KW is converted in (single) pass of the reaction gas mixture stream through the second third of the amount M in flow direction, and a proportion of C mol % of the molar starting amount KW of the hydrocarbon to be dehydrogenated is converted to dehydrogenated hydrocarbon in (single) pass of the reaction gas mixture stream through the last third of the amount M in flow direction, with the proviso that a total of G=(A+B+C) mol % of the molar starting amount KW of hydrocarbon to be dehydrogenated present therein is dehydrogenated to dehydrogenated hydrocarbon in (single) pass of the reaction gas mixture stream through the overall catalyst bed, and, if appropriate, streams of molecular oxygen, molecular hydrogen, steam and/or other inert gas are supplied as dehydrogenation auxiliary gases to the reaction gas mixture stream between its entry into the start of the overall catalyst bed and its exit from the end of the overall catalyst bed, and the deactivation of the overall catalyst bed which accompanies increasing operating time in an operating time interval of $t_0<t<t_R$, where $t_R$ is the operating time t at which the dehydrogenation is interrupted and the overall catalyst bed is regenerated for the first time after the operating time $t=t_0$, is counteracted by varying the profile of the temperature of the reaction gas mixture stream within the overall catalyst bed and/or the stream of any dehydrogenation auxiliary gases supplied, which comprises performing the variation in such a way that, with increasing operating time t, proportion A decreases, proportion B passes through a maximum and proportion C increases.

It will be appreciated that, on the industrial scale, the partial conversions A, B, C in the process according to the invention may be subject to certain variations for various reasons. In this case, the actual profile of the partial conversions A, B, C over the operating time is plotted and a fitted curve is drawn in each case through the measurement points by the method of least mean squares developed by Legendre and Gauss. When this fitted curve, over the operating time interval $t_0<t<t_R$, decreases for the partial conversion A and increases for the partial conversion C and passes through a maximum for the partial conversion B, the inventive profile of requirements is satisfied. Interruptions to the process according to the invention are not taken into account in the fitted curves.

The fitted curve is decreasing in the relevant operating time interval for the partial conversion A when A either decreases continuously with increasing t over the operating time interval on the fitted curve for A, or (over the operating time interval) decreases but may temporarily remain constant.

The fitted curve is increasing in the relevant operating time interval for the partial conversion C when C either increases continuously with increasing t over the operating time interval on the fitted curve for C, or (over the operating time interval) increases but may temporarily remain constant.

The fitted curve passes through an (absolute) maximum in the relevant operating time interval for the partial conversion B when there is exactly one operating time $t_{max}$ within this operating time interval at which, firstly, the value of the first derivative of the fitted curve has the value "0", and, secondly, the partial conversion values B on the fitted curve for the operating times $t<t_{max}$ are less than the partial conversion B at the operating time $t_{max}$, and the partial conversion values B on the fitted curve for the operating times $t>t_{max}$ are less than and/or equal to (i.e. the partial conversion B at the operating time $t_{max}$.

Appropriately in accordance with the invention, the operating time $t=t_0$ in the process according to the invention for heterogeneously catalyzed partial dehydrogenation is that operating time of a freshly charged or freshly regenerated overall dehydrogenation catalyst bed at which the process operation attains its steady operating state essentially for the first time, which is normally characterized in that, based on single pass of the reaction mixture through the overall dehydrogenation catalyst bed, G mol % of the molar starting amount KW of the hydrocarbon to be dehydrogenated present in the reaction gas mixture is converted to dehydrogenated hydrocarbon. In principle, the operating time $t_O$ may also be beyond this operating time in the process according to the invention.

Appropriately from an application point of view, the partial conversion A in the process according to the invention at the operating time $t=t_0$, (based on the overall conversion $G=(A+B+C)$, is from 45 to 80 (or to 75) %, the partial conversion B from 20 to 40% and the partial conversion C from 0 to or from 5 to 15%.

Preferably in accordance with the invention, the partial conversion A in the process according to the invention at the operating time $t=t_0$, based on the overall conversion $G=(A+B+C)$, is from 55 to 70%, the partial conversion B from 25 to 35% and the partial conversion C from 7 to 13%.

More preferably in accordance with the invention, the partial conversion A in the process according to the invention at the operating time $t=t_0$, based on the overall conversion $G=(A+B+C)$, is from 55 to 65%, the partial conversion B from 27 to 33% and the partial conversion C from 8 to 12%.

The value of the overall conversion G in mol % in (single) pass of the reaction gas mixture stream through the overall catalyst bed, based on the molar starting amount KW of hydrocarbon to be dehydrogenated present in the reaction gas mixture stream, total amount of hydrocarbon to be dehydrogenated converted to dehydrogenated hydrocarbon, in the process according to the invention within the operating time interval $t_0<t<t_R$, normally remains constant within the range of $G\pm5$ mol %, preferably $G\pm4$ mol %, or $G\pm3$ mol %, and more preferably $G\pm2$ mol %, or $G\pm1$ mol %, and most preferably $G\pm0.75$ mol % or $G\pm0.50$ mol % and even better $G\pm0.25$ mol % or $G\pm0.1$ mol %.

According to the invention, it is also favorable when, within the operating time interval $t_0<t<t_R$, the partial conversion A falls below the partial conversion C with increasing operating time, so that C>A after a certain operating time. In many cases, it is even advantageous in the process according to the invention when the sequence of the partial conversions A, B, C is reversed within the relevant operating time interval, so that, after a certain operating time, it is no longer the case that A>B>C, but rather C>B>A.

In general, the partial conversion value A in the process according to the invention does not, however, go below the 20% mark, preferably not below the 30% mark, based on the partial conversion value A at the operating time $t=t_0$. In other words, the process is normally interrupted before it goes below this value and the overall dehydrogenation catalyst bed is regenerated (in this way, the irreversible deactivation part is normally kept to a minimum). Moreover, generally neither of the partial conversion values B, C in the process according to the invention (typically for the aforementioned reasons) exceeds the 95% mark, preferably the 85% mark, based on the partial conversion value A at the operating time $t=t_0$.

In general, in the process according to the invention, however, both the partial conversion value B and the partial conversion value C exceed the 50% mark based on the partial conversion value A at the operating time $t=t_0$.

G in the process according to the invention will normally be from 5 to or from 10 to 60 mol %, frequently from 10 to 50 mol %, in many cases from 15 to 40 mol %, or from 15 to 30 mol %, or from 15 to 25 mol %.

In addition, the process according to the invention can be applied to all processes for the heterogeneously catalyzed partial dehydrogenation of hydrocarbon detailed in the preamble of this document.

In other words, useful dehydrogenation catalysts for the overall catalyst bed of the process according to the invention are in principle all dehydrogenation catalysts known in the prior art for heterogeneously catalyzed dehydrogenations. They can be divided roughly into two groups, specifically into those which are of oxidic nature (for example chromium oxide and/or aluminum oxide) and into those which consist of at least one generally comparatively noble metal (for example an element from the platinum group, for example platinum and/or palladium) deposited on a generally oxidic support (for example zirconium dioxide, aluminum oxide, silicon dioxide, titanium dioxide, magnesium oxide, lanthanum oxide and/or cerium oxide). The dehydrogenation catalysts used may thus include all of those recommended in WO 01/96270, EP-A 731 077, DE-A 102 11 275, DE-A 101 31 297, WO 99/46039, U.S. Pat. No. 4,788,371, EP-A 705 136, WO 99/29420, U.S. Pat. No. 4,220,091, U.S. Pat. No. 5,430,220, U.S. Pat. No. 5,877,369, EP-A 117 146, DE-A 199 37 196, DE-A 199 37 105, U.S. Pat. No. 3,670,044, U.S. Pat. No. 6,566,573 and WO 94/29021. Further dehydrogenation catalysts suitable for the process according to the invention are present in WO 01/83405.

In principle, either the overall catalyst bed or a partial catalyst bed may consist exclusively of dehydrogenation catalyst. It will be appreciated that it is also possible for either the overall catalyst bed or a partial catalyst bed to comprise the dehydrogenation catalyst in a form diluted with inert material.

Since the overall catalyst bed for the process according to the invention is preferably a fixed bed (alternatives are, for example, the fluidized bed and the moving bed) (all statements made in this document apply in particular to the fixed bed variant), a dehydrogenation catalyst in this document shall be understood in particular to mean a shaped body whose longest dimension L (longest line connecting two points on the surface of the shaped body) is from 0.1 or 1 to 30 mm, preferably from 1 to 20 mm and more preferably from 1 to 10 mm or from 1 to 5 mm, and which, in the experiment described below, based on single pass of the reaction gas mixture through the reaction tube, dehydrogenates at least 5 mol % of the propane present in the reaction gas to propylene:

A reaction tube made of steel of EN materials number 1.4835 with a wall thickness of 2 mm and an internal diameter of 35 mm and a length of 80 cm is filled as follows: 50 ml of a bed of the appropriate dehydrogenation catalyst are placed centrally in the reaction tube. Above and below the bed of shaped catalyst bodies, the reaction tube is filled up in each case with a bed of steatite spheres (inert spheres) having a sphere diameter of from 1.5 to 2.5 mm. A grid bears the entire bed. From the outside, the reaction tube is kept at a temperature of 550° C. over its entire length. The reaction tube is charged with a mixture of propane and steam in a volume ratio of 2 (propane) to 1 (steam) with a propane loading of the bed of shaped catalyst bodies of 1000 l (STP)/l·h. The reaction gas mixture stream conducted into the reaction tube is preheated to a temperature of 550° C. For the process according to the invention, particular preference is given to dehydrogenation catalysts for which, under the aforementioned boundary conditions, the cumulative selectivity of formation of the ethane, ethylene and methane by-products is ≤5 mol % based on propane converted.

In this document, the loading of a catalyst bed catalyzing a reaction step with reaction gas shall be understood quite generally to mean the amount of reaction gas in standard liters (equals l (STP); the volume in liters that the corresponding amount of reaction gas would take up under standard conditions (0° C., 1 atm)) which is conducted through one liter of catalyst bed per hour. However, the loading may also be based on only one constituent of the reaction gas. In that case, it is the amount of this constituent in l (STP)/l·h which is conducted through one liter of the catalyst bed per hour (pure inert material beds are not counted in a fixed catalyst bed). The loading may also be based only on the amount of catalyst present in one catalyst bed which comprises the actual catalyst diluted with inert material (this is then stated explicitly).

In principle, the process according to the invention can be operated at loadings on the overall catalyst bed (based on the total amount M of dehydrogenation catalyst present therein), either with reaction gas or with the hydrocarbon to be dehydrogenated (e.g. propane) present therein, of from 100 to 10 000 h$^{-1}$ (l (STP)/l·h, abbreviated to h$^{-1}$), frequently from 300 to 5000 h$^{-1}$, i.e. in many cases from 500 to 3000 h$^{-1}$ (essentially irrespective of the desired conversion of hydrocarbon to be dehydrogenated).

Useful inert materials for the dilution of the dehydrogenation catalyst in the overall catalyst bed and/or partial catalyst bed are, for example, fired clays (aluminum silicates) or steatite (e.g. type C 220 from CeramTec), or other high-temperature chemicals (preferably essentially free of pores) such as aluminum oxides, silicon dioxide, titanium dioxide, magnesium oxide, lanthanum oxide, cerium oxide, zinc aluminum mixed oxide, thorium dioxide, zirconium dioxide, silicon carbide or other silicates such as aluminum and/or magnesium silicate and mixtures of the aforementioned materials. Shaped bodies made from the aforementioned materials are, though, not just useful in the process according to the invention for the dilution of the overall fixed catalyst bed and/or of partial fixed catalyst beds, but also as an inert top bed and, if appropriate, concluding bed of the overall fixed catalyst bed and/or of partial fixed catalyst beds.

Advantageously, such an inert top bed and/or concluding bed of inert shaped bodies in the process according to the invention should be such that ≤3 mol %, better ≤2 mol %, even better ≤1 mol % or 0 mol % of the hydrocarbon to be dehydrogenated present in the reaction gas mixture stream is converted to dehydrogenated hydrocarbon as the stream passes through this inert bed.

In particular, the dehydrogenation catalysts used for the overall catalyst bed for the process according to the invention may be the catalysts according to example 1, example 2, example 3 and example 4 of DE-A 199 37 107.

These dehydrogenation catalysts comprise from 10 to 99.9% by weight of zirconium dioxide, from 0 to 60% by weight of aluminum oxide, silicon dioxide and/or titanium dioxide, and from 0.1 to 10% by weight of at least one element of the first or second main group, of an element of the third transition group, of an element of the eighth transition group of the Periodic Table of the Elements, lanthanum and/or tin, with the proviso that the percentages by weight add up to 100% by weight.

In a preferred embodiment, aforementioned dehydrogenation catalysts comprise at least one element of transition group VIII, at least one element of main group I and II, at least one element of main group III and/or IV and at least one element of transition group III including lanthanides and actinides. As the element of transition group VIII, the active composition of the dehydrogenation catalysts preferably comprises platinum and/or palladium, more preferably platinum. As elements of main group I and II, the active composition of the aforementioned dehydrogenation catalysts preferably comprises potassium and/or cesium. As elements of transition group III including the lanthanides and actinides, the active composition of the aforementioned dehydrogenation catalysts preferably comprises lanthanum and/or Cr. As elements of main group III and/or IV, the active composition of the aforementioned dehydrogenation catalysts preferably comprises one or more elements from the group consisting of boron, gallium, silicon, germanium, indium, tin and lead, more preferably tin. Most preferably, the active composition of the aforementioned dehydrogenation catalysts in each case comprises at least one representative of the aforementioned element groups.

Generally, the dehydrogenation catalyst for an overall fixed catalyst bed and/or partial fixed catalyst bed may comprise catalyst extrudates (diameter typically from 0.1 or 1 to 10 mm, preferably from 1.5 to 5 mm; length typically from 1 to 20 mm, preferably from 3 to 10 mm), tablets (preferably the same dimensions as for the extrudates), and/or catalyst rings (external diameter and length in each case typically from 2 to 30 mm or to 10 mm, wall thickness appropriately from 1 to 10 mm, or to 5 mm, or to 3 mm).

In principle, there exist no restrictions for use in the fixed bed either with regard to the catalyst geometry (especially in the case of supported catalysts) or with regard to the geometry of the inert shaped bodies. Particularly frequent geometries are solid cylinders, hollow cylinders (rings), spheres, cones, pyramids and cubes, and also extrudates, wagonwheels, stars and monoliths.

The longest dimension of the shaped catalyst bodies and of the shaped inert bodies (longest line connecting two points on the shaped body surface) may be from 0.5 mm to 100 mm, often from 1.5 mm to 80 mm and in many cases from 3 mm to 50 mm or to 20 mm.

Finally, the dehydrogenation catalysts of German application 10 2005 044 916 should also be recommended as particularly suitable for an inventive overall fixed catalyst bed and/or partial fixed catalyst bed.

The regeneration of the dehydrogenation catalysts recommended for the process according to the invention can in particular be effected in such a way that, at an entrance temperature of from 300 to 600° C. (in extreme cases, if appropriate, even up to 750° C.), frequently from 400 to 450° C., air diluted (preferably) with molecular nitrogen and/or steam is initially passed through the overall (fixed) catalyst bed in first regeneration stages. The catalyst loading with regeneration gas may (based on the total amount of dehydrogenation catalyst M), for example, be from 50 to 10 000 h$^{-1}$ and the oxygen content of the regeneration gas from 0.1 or 0.5 to 20% by volume. In subsequent further regeneration stages, the regeneration gas used under otherwise identical regeneration conditions may be air. Appropriately from an application point of view, it is advisable to flush the overall (fixed) catalyst bed comprising the dehydrogenation catalyst, before the start of the regeneration, with inert gas (e.g. N$^2$, e.g. industrial nitrogen with up to 1% by volume of $O_2$, $H_2O$ or mixtures thereof). As a conclusion to the regeneration, it is generally advisable to regenerate the overall catalyst bed with pure molecular hydrogen (purity >99% by volume) or with molecular hydrogen diluted with inert gas (preferably steam and/or nitrogen) (the hydrogen content should be ≥1% by volume) under otherwise identical conditions.

In principle, the reaction zone RZ in the process according to the invention may comprise only one dehydrogenation reactor or a plurality of dehydrogenation reactors. These may be operated in series and/or parallel connection. Correspondingly, the overall catalyst bed may be present in only one dehydrogenation reactor or distributed in the form of partial catalyst beds between a plurality of reactors. When the overall catalyst bed is present in only one dehydrogenation reactor, it may in principle be only one catalyst bed continuous without interruption in flow direction.

In this case, the overall catalyst bed may also have interruptions in the overall composition in flow direction caused by pure concluding and/or preliminary inert material beds (for example beds of shaped bodies). The overall catalyst bed may also, for example, consist of partial fixed beds arranged in series radially or axially in a reactor, between which there is intermediate space free of solids. This is the case, for example, when the reaction zone RZ is a staged reactor. It will be appreciated that a reaction zone may also comprise a plurality of staged reactors. However, it may also consist of a reactor connection which comprises one or more dehydrogenation reactors which comprise only one partial dehydrogenation catalyst bed (for example a partial fixed dehydrogenation catalyst bed), and one or more dehydrogenation reactors which comprise more than one partial dehydrogenation catalyst bed (for example in the form of partial fixed catalyst bed stages).

In order to counteract, in accordance with the invention, the deactivation of the overall catalyst bed accompanying increasing operating time within an operating time interval $t_0 < t < t_R$, useful methods of external and internal control of the temperature of the reaction gas mixture on its way through the overall catalyst bed are primarily all of those already described in the preamble of this document, including the adjustment of the temperature of the reaction gas mixture stream which comprises the molar starting amount KW of the hydrocarbon to be dehydrogenated and enters the overall catalyst bed. In principle, it is, though, also possible to employ partial pressure change by, for example, varying the inert gas dilution. Frequently, the different possible control methods may also be employed together. This also includes the removal of the $H_2$ reaction product.

In a simple manner, the inventive aim can be achieved, for example, by configuring the overall catalyst bed in the process according to the invention adiabatically both within the first third of the total amount M of dehydrogenation catalyst present in the overall fixed catalyst bed in flow direction of the reaction gas mixture stream and within the second and last thirds of this amount M in flow direction, but with the possibility of changing the heat content of the reaction gas mixture before entry into the particular adiabatic third.

Appropriately from an application point of view, the procedure at the operating time $t_0$ will be that the temperature $T_1$ of the reaction gas mixture on entry into the first third of the amount M in flow direction is greater than the temperature $T_2$ of the reaction gas mixture on entry thereof into the second third of the amount M, and $T_2$ is greater than the temperature $T_3$ of the reaction gas mixture on entry thereof into the last third of the amount M in flow direction.

The increasing deactivation of the overall catalyst bed within the operating time interval $t_0 < t < t_R$ can be counteracted in a simple manner in accordance with the invention by increasing both $T_1$, and $T_2$ and $T_3$, in a mutually balanced manner in the context of the inventive objective. The temperature growth rate of $T_3$ is normally constantly above the temperature growth rate of $T_1$. The temperature growth rate of $T_2$ is, in contrast, normally initially above the temperature growth rate of $T_3$ to fall below the temperature growth rate of $T_3$ in further operation and to approximate ever more closely to the lower growth rate of $T_1$.

In the manner described above, not only is the desired molar fraction G (expressed in mol % of KW) of KW converted in the (single) pass of the reaction gas mixture stream comprising the hydrocarbon to be dehydrogenated in a molar starting amount KW through the overall catalyst bed to dehydrogenated hydrocarbon maintained essentially unchanged for as long as possible, but the deactivation resulting from this operating mode can to a very large extent be removed again over a comparatively long-lasting operating time in a dominantly reversible manner, i.e. by subsequent use of the regeneration processes already described.

An essential feature of the invention is that the real degree of dilution of the different third portions of the total amount M of dehydrogenation catalyst with inert material in the real overall catalyst bed in the inventive procedure (especially in the process variants just described) may be either identical or different. In principle, all third portions of M may also be present undiluted in the overall catalyst bed. It will be appreciated that the degree of dilution of the dehydrogenation catalyst may also vary within a third portion of M in flow direction.

In a certain manner, the process according to the invention is designed in such a way that the contribution to G, caused by a portion of M of any size in flow direction, normalized to this (i.e. divided by this) portion passes through a maximum with the proviso that the site of this normalized maximum contribution to G, over the inventive long-term operation in the $t_0 < t < t_R$ operating time interval, with increasing operating time t, passes through the overall dehydrogenation catalyst bed starting from the inlet into the overall catalyst bed toward the outlet of the reaction gas mixture stream (of the product gas mixture stream) out of the overall catalyst bed.

In a particularly simple manner, the inventive long-term operating mode just described is realizable in an adiabatic staged reactor. The particular partial catalyst bed in the reaction chamber may be a fluidized bed, or a moving bed, or a fixed bed. It will be appreciated that fluidized bed and, for example, fixed bed, or moving bed and fixed bed, or any other combination of the catalyst bed types mentioned may also be present in combination in the reaction chamber. In a manner appropriate from an application point of view, the reaction gas mixture stream is then subjected to the intermediate heating required for this inventive process variant in the otherwise adiabatic staged reaction chamber on its way from one partial catalyst bed stage to the next partial catalyst bed stage, for example by passing it over heat exchanger ribs heated by means of hot gases or steam, or by passing it through tubes heated with hot combustion gases or steam, or heat exchanger plates heated with hot gases. In a corresponding manner, it is also possible to vary the temperature of the reaction gas mixture stream which comprises the starting amount KW and is supplied to the inlet into the overall catalyst bed. In a particularly simple manner, the staged reactor will comprise three identical catalyst stages. In principle, the staged reactor may also comprise six, or nine, or twelve, or another number of identically or differently charged catalyst stages. An intermediate heating may be undertaken between all successive stages or only between some successive stages.

Particularly appropriately from an application point of view, the aforementioned staged reactor may be a pure fixed catalyst bed staged reactor. In the simplest case, the partial catalyst beds in the reaction chamber are arranged in a number of stages corresponding to the number of partial fixed beds in axial succession in flow direction of the reaction gas mixture stream or in spatial succession in the annular gaps of concentric cylindrical grids. However, it is also possible to arrange the annular gaps in the reaction chamber in segments one on top of another and to conduct the reaction gas mixture stream, after radial passage in one segment, into the next segment above it or below it. In the simplest form, the partial (fixed) catalyst bed stages are accommodated in an adiabatic shaft furnace reactor.

Preferably in accordance with the invention, a bed of inert shaped bodies is present both upstream and downstream of a partial fixed catalyst bed in a staged fixed bed reactor used for the process according to the invention. This is firstly because the shaped dehydrogenation catalyst bodies frequently have a smaller dimension than the mesh width of the accompanying (support) grid. This can be counteracted by means of a downstream bed of inert shaped bodies of suitable size.

A bed of inert bodies upstream in flow direction is found to be advantageous, inter alia, from the point of view of a very homogeneous (both in relation to temperature and reaction gas mixture composition) reaction gas mixture stream. This is especially true when the reaction gas mixture stream supplied to the partial fixed catalyst bed has been obtained by combining various individual gas streams.

The latter is of significance, for example, when the indirect temperature control to be employed between the partial dehydrogenation catalyst beds for the above-described embodiment of the process according to the invention is replaced at least partly by direct temperature control. Preferably from an application point of view, a variation of the temperature control to be employed between two partial catalyst beds is realized in the process according to the invention exclusively via the route of direct temperature control.

To this end, a gas comprising molecular oxygen is added to the reaction gas mixture stream on its inventive route through the reaction zone RZ, for example after it has flowed through the first partial catalyst bed and, if appropriate, between the downstream partial catalyst beds to a limited extent varying over the operating time of the process according to the invention.

This may be, for example, pure molecular oxygen or a mixture of inert gas and molecular oxygen (for example air). Depending on the dehydrogenation catalyst used, as already detailed in the preamble to this document, restricted combustion, which varies in a corresponding manner, of the hydrocarbons present in the reaction gas mixture, if appropriate carbon or carbon-like compounds already deposited on the catalyst surface and/or of hydrogen formed in the course of the conventional heterogeneously catalyzed dehydrogenation (for example of a propane dehydrogenation) and/or added to the reaction gas is brought about in this way (it may also be appropriate from an application point of view to include catalyst beds in the staged reaction chamber (in the reaction zone RZ) which are charged with catalyst which specifically (selectively) catalyzes the combustion of hydrogen (and/or of hydrocarbon) (useful such catalysts include, for example, those of the documents U.S. Pat. No. 4,788,371, U.S. Pat. No. 4,886,928, U.S. Pat. No. 5,430,209, U.S. Pat. No. 5,530,171, U.S. Pat. No. 5,527,979 and U.S. Pat. No. 5,563,314; for example, such catalyst beds may be accommodated in an alternating manner to the beds comprising dehydrogenation catalyst in the staged reaction chamber)). The variation in the heat of reaction released by the restricted combustion, which accompanies it in accordance with the variation of the amount of molecular oxygen metered in, then causes the variation in the dehydrogenation conversion proportions required in accordance with the invention. In contrast, appropriately from an application point of view, the oxygen content of the reaction gas mixture stream comprising the starting amount KW of hydrocarbon to be dehydrogenated will typically be kept constant in the course of an inventive long-term operation and only the temperature of this (input) reaction gas mixture stream will be varied (generally by indirect heat exchange). However, the measure of direct temperature control cannot only be employed in the case of a staged reactor as reaction zone RZ. Instead, it can also be employed in the case of a single dehydrogenation catalyst bed uninterrupted in flow direction of the reaction gas mixture stream in the reaction zone RZ. This is possible in a simple manner from an application point of view, for example, by having introduced oxygen metering probes (lances) into the, for example, fixed catalyst bed at different catalyst bed lengths, through which a gas comprising molecular oxygen can be supplied to the reaction gas mixture stream. In a simple manner, the inventive aim can therefore also be achieved by configuring the overall catalyst bed in the process according to the invention both in the extent of the first thirds of the total amount M of dehydrogenation catalyst present in the overall catalyst bed in flow direction of the reaction gas mixture stream, and in the extent of the second and last third of this amount M in flow direction, but with the possibility of changing the heat content of the reaction gas mixture before entry into the first adiabatic third in flow direction by indirect temperature control and, on entry into the second and third adiabatic third in flow direction, by direct temperature control (for example by variation of the stream of gas comprising molecular oxygen supplied to it in each case before entry of the reaction gas mixture stream into the second or third adiabatic third).

Appropriately from an application point of view, the procedure at the operating point $t_0$ will then be that the highest temperature $T_1^*$ of the reaction gas mixture stream as it flows through the first third of the amount M in flow direction is greater than the highest temperature $T_2^*$ of the reaction gas mixture stream as it flows through the second third of the amount M in flow direction, and $T_2^*$ is greater than the maximum temperature $T_3^*$ of the reaction gas mixture stream as it flows through the last third of the amount M in flow direction.

The setting of $T_1^*$ is possible in a simple manner by adjusting the content of heat and molecular oxygen in the reaction gas mixture stream on entry thereof into the first third of the amount M in flow direction. The relative position of $T_2^*$ and $T_3^*$, both with respect to one another and with respect to $T_1^*$, is then determined by the streams of gas comprising molecular oxygen metered into the reaction gas mixture stream between the first and second third of the amount M in flow direction and between the second and last (third) third of the amount M in flow direction. In a simple manner, the same gas comprising molecular oxygen (for example pure molecular oxygen (purity ≥99% by volume), or air or another mixture of inert gas and molecular oxygen) will be used in both cases. The desired relative position of $T_2^*$, $T_3^*$ with respect to one another at the operating time $t=t_0$ is typically obtained in a particularly simple manner when the streams of molecular oxygen metered in at this operating time are selected identically.

The increasing deactivation of the overall catalyst bed in the $t_0 < t < t_R$ operating time interval can now be counteracted in a simple manner in accordance with the invention by increasing, in a mutually adjusted manner in the context of the inventive objective, both the heat content (the temperature) of the reaction gas mixture stream on entry thereof into the first third of the amount M in flow direction and the streams of molecular oxygen (or of gas comprising it) metered in between the first and second third of the amount M in flow direction (stream 1) and between the second and last (third) third of the amount M in flow direction (stream 2).

The growth rates in streams 1 and 2 of molecular oxygen are initially selected to be largely identical. Subsequently, the growth rate of stream 2 of molecular oxygen is above that of stream 1 of molecular oxygen before the growth rate of stream 1 of molecular oxygen exceeds that of stream 2 of molecular oxygen, and stream 2 of molecular oxygen declines below stream 1 of molecular oxygen. Overall, streams 1, 2 of molecular oxygen (each calculated net) over the $t_0 < t < t_R$ operating time interval, in comparison to the temperature of the reaction gas mixture stream on entry thereof into the first third of the amount M in flow direction, are increased in such a way that the temperature growth rate of $T_3^*$ is essentially constantly above the temperature growth rate of $T_1^*$. The temperature growth rate of $T_2^*$ is, in contrast, normally initially above the temperature growth rate of $T_3^*$ to fall below the temperature growth rate of $T_3^*$ in the further course of operation and to approximate ever closer to the lower growth rate of $T_1^*$.

In a particularly simple manner, the inventive long-term operating mode just described is realizable in an adiabatic staged reactor, especially in a staged fixed catalyst bed reactor. Appropriately in accordance with the invention, the staged fixed catalyst bed reactor has three, preferably identical fixed catalyst bed stages (partial fixed catalyst beds). The oxygen feeding can be effected between the fixed catalyst bed stages. The partial fixed dehydrogenation catalyst beds may be arranged in axial succession in flow direction of the reaction gas mixture stream or in spatial succession in the annular gaps of concentric cylindrical grids. In a particularly simple manner, an adiabatic shaft furnace reactor is used, as described, for example, in German application 10 2006 015 235, German application 10 2006 017 623, German application 10 2006 029 790 and in DE-A 10 2005 051 401.

In order to keep the streams supplied overall in the course of intermediate oxygen feeding essentially constant over the operating time, the gas comprising molecular oxygen metered in, advantageously from an application point of view, comprises steam as an inert accompanying diluent gas. An increasing oxygen flow rate is then advantageously accompanied by a decreasing steam flow rate, so that the total stream of gas comprising oxygen supplied overall remains essentially constant (over the operating time).

Advantageously in accordance with the invention, intermediate feeding of a gas comprising molecular oxygen is undertaken in such a way that homogeneous mixing thereof with the reaction gas mixture stream at the metering point forms a new reaction gas mixture in which the molar ratio of molecular oxygen present to molecular hydrogen present is $\leq 1:2$. The compliance with this boundary condition ensures increased target product selectivity.

It is surprising that the temperature control required to realize an inventive long-term operating mode, in spite of the aforementioned boundary condition, is possible essentially without loss of target product selectivity even by the route of direct temperature control to be employed as described without necessarily requiring supply of external molecular hydrogen. When an increased content of molecular hydrogen is required in the aforementioned context, it can be adjusted, appropriately in accordance with the invention, also by employing the loop mode described in the documents WO 03/076370 and DE-A 102 11 275, in which the product gas stream withdrawn from the reaction zone RZ is divided into two portions of identical composition and one of the two portions is recycled into the reaction zone RZ as dehydrogenation cycle gas to charge it. A heterogeneously catalyzed partial dehydrogenation with loop mode is also disclosed by WO 2006/050957. If required, external molecular hydrogen can also be supplied to the reaction gas mixture stream in the process according to the invention. Especially when value is placed on an increased lifetime of the overall catalyst bed, it is advantageous in accordance with the invention to add molecular hydrogen actually to the reaction gas mixture stream supplied to the reaction zone RZ. This is true especially when the aforementioned reaction gas mixture stream comprises molecular oxygen. This is generally the case especially when the process according to the invention is followed by a process for heterogeneously catalyzed partial oxidation of dehydrogenated hydrocarbon obtained (for example propylene to acrolein and/or acrylic acid) accompanied by unconverted hydrocarbon to be dehydrogenated (e.g. propane) as an inert gas in the partial oxidation, and the procedure is as follows:

First, the product gas stream withdrawn from the reaction zone RZ will be used as such or after removal of at least a portion of its constituents (e.g. $H_2$, $H_2O$, $N_2$, etc.) other than the dehydrogenated hydrocarbon (e.g. propylene) and the (unconverted) hydrocarbon to be dehydrogenated (e.g. propane) to charge at least one oxidation reactor, and the dehydrogenated hydrocarbon present in the charge gas mixture (e.g. propylene) will be subjected to a selective heterogeneously catalyzed partial gas phase oxidation with molecular oxygen to give a partial oxidation product gas mixture comprising the (partial oxidation product) target product (for example acrolein or acrylic acid or a mixture thereof), and also generally unconverted hydrocarbon to be dehydrogenated (e.g. propane), excess molecular oxygen and, if appropriate, unconverted dehydrogenated hydrocarbon (e.g. propylene).

In a downstream separation zone, target product (for example acrolein or acrylic acid or a mixture thereof) present in the partial oxidation product gas mixture will be removed and, from the remaining residual gas comprising unconverted hydrocarbon to be dehydrogenated (e.g. propane), molecular oxygen and, if appropriate, unconverted dehydrogenated hydrocarbon (e.g. propylene), at least a portion comprising unconverted hydrocarbon to be dehydrogenated (e.g. propane) and usually unconverted molecular oxygen and, if appropriate, unconverted dehydrogenated hydrocarbon (e.g. propylene) will be recycled into the process according to the invention as partial oxidation cycle gas (generally as a constituent of the reaction gas mixture stream which is supplied to the reaction zone RZ and comprises the starting amount KW of hydrocarbon to be dehydrogenated).

When the process according to the invention (but also otherwise) is, for example, a heterogeneously catalyzed partial dehydrogenation of propane to propylene, and the partial oxidation which follows is that of propylene to acrolein or to acrylic acid or to a mixture thereof, the reaction gas mixture stream supplied to the reaction zone RZ may comprise, for example, as significant contents:

from $\geq 0$ to 20 or to 10, frequently from 0 to 6% by volume of propylene, from $\geq 0$ to 1, in many cases from 0 to 0.5, frequently from 0 to 0.25%, preferably from 0 to 0.05% by volume of acrolein, from $\geq 0$ to 0.25 (or to 0.4), in many cases from $\geq 0$ to 0.05, frequently from $\geq 0$ to 0.03% by volume of acrylic acid, from $\geq 0$ to 20 or to 5, in many cases from $\geq 0$ to 3, frequently from $\geq 0$ to 2% by volume of $CO_y$, from 5 to 50, preferably from 20 to 40% by volume of propane, from 20 or 30 to 80, preferably from 50 to 70% by volume of nitrogen, from $\geq 0$ to 5, preferably from 1.0 to 2.0% by volume of oxygen, from $\geq 0$ to 20, preferably from 5.0 to 10.0% by volume of $H_2O$, and from $\geq 0$, frequently from $\geq 0.01$, often from $\geq 0.05$ to 10, preferably from 1 to 5% by volume of $H_2$.

Acetic acid may also be present in small amounts (approximately comparable to the possible acrylic acid contents).

Typically, target product (for example acrylic acid) is removed from the partial oxidation product gas mixture by converting the target product (for example the acrylic acid) to the condensed phase. This can be done by absorptive and/or condensative (cooling) measures. Useful absorbents in the case of acrylic acid as the target product are, for example, water, aqueous solutions or high-boiling ($T_{boil}$ of solvent >$T_{boil}$ of acrylic acid at 1 atm), especially hydrophobic, organic solvents. More preferably, the conversion to the condensed phase in the case of acrylic acid is effected by fractional condensation of the partial oxidation product gas mixture. Preference is given to effecting the absorptive and/or condensative conversion of acrylic acid from the partial oxidation product gas mixture to the condensative phase in columns comprising separating internals, in which the partial oxidation product gas mixture is normally conducted ascending from the bottom upward. The absorbent is generally introduced at the top of the column, at which the residual gas is normally released from the column.

The further removal of the acrylic acid from the condensed phase is effected generally in the desired purity using at least one thermal separation process. This is understood to mean those processes in which at least two different substance phases (for example liquid/liquid; gaseous/liquid; solid/liquid; gaseous/solid, etc.) are obtained and contacted with one another. Owing to the gradients existing between the phases, heat and mass transfer takes place between them and ultimately causes the desired separation (removal). The term "thermal separation process" reflects that it requires either the withdrawal or the supply of heat to obtain the formation of the substance phases and/or that the withdrawal or the supply of thermal energy promotes or maintains the mass transfer. Preferably in accordance with the invention, the at least one thermal separation process comprises at least one crystallizative removal from liquid phase. Appropriately in accordance with the invention, the at least one crystallizative removal of acrylic acid is a suspension crystallization, and the suspension crystals are advantageously washed with molten crystals which have been removed beforehand and washed in a wash column (a gravimetric, or a mechanical, or a hydraulic wash column; preference is given in accordance with the invention to the latter). Otherwise, useful thermal separation processes are, for example, extractive, desorptive, cristallizative, rectificative, azeotropically distillative, azeotropically rectificative, distillative and/or stripping processes. In general, pure acrylic acid will be obtained by employing combinations of different thermal separation processes of those mentioned.

The removal of acrylic acid described can be followed by a process for free-radical polymerization (especially for preparing water-superabsorbent polyacrylic acids and/or their partly or fully neutralized alkali metal (preferably Na) salts), in which acrylic acid removed is polymerized free-radically to prepare polymers.

It is also possible for the removal of acrylic acid described to be followed by a process for preparing acrylic esters, in which removed acrylic acid is esterified with alcohols (preferably alkanols, more preferably $C_1$- to $C_{12}$-alkanols) (generally under acid catalysis).

The process for esterification may in turn be followed by a process for free-radical polymerization, in which acrylic ester thus prepared is polymerized.

Disregarding the peculiarity of the inventive long-term operating mode, processes according to the invention for preparing propylene from propane as the propylene source for partial oxidations thereof to prepare acrolein and/or acrylic acid are known, including a cycle gas method of oxidation cycle gas and, if appropriate, dehydrogenation cycle gas. For example, descriptions of such multistage processes can be found in the documents DE-A 10 2005 022 798, DE 10 2006 024 901.1, DE-A 102 46 119, DE-A 102 45 585, DE-A 10 2005 049 699, DE-A 10 2004 032 129, DE-A 10 2005 013 039, DE-A 10 2005 010 111, DE-A 10 2005 009 891, DE-A 102 11 275, EP-A 117 146, U.S. Pat. No. 3,161,670, DE-A 33 13 573, WO 01/96270, DE-A 103 16 039, DE-A 10 2005 009 885, DE-A 10 2005 052 923, DE-A 10 2005 057 197, WO 03/076370, DE-A 102 45 585, DE-A 22 13 573, U.S. Pat. No. 3,161,670 and the prior art cited in these documents. DE-A 102 19 686 discloses the corresponding procedure in the case of preparation of methacrolein and/or methacrylic acid.

Detailed descriptions of absorptive and/or condensative processes for converting acrylic acid from a partial oxidation product gas mixture into the condensed phase can likewise be found in the prior art. This includes the documents DE-A 103 36 386, DE-A 196 31 645, DE-A 195 01 325, EP-A 982 289, DE-A 198 38 845, WO 02/076917, EP-A 695 736, EP-A 778 225, EP-A 1 041 062, EP-A 982 287, EP-A 982 288, US-A 2004/0242826, EP-A 792 867, EP-A 784 046, EP-A 695 736 (especially absorptive) and WO 04/035514, DE-A 199 24 532, DE-A 198 14 387, DE-A 197 40 253, DE-A 197 40 252 and DE-A 196 27 847 (especially condensative).

In addition, descriptions of such absorptive and/or condensative removals of acrylic acid from partial oxidation product gas mixtures can also be found in the documents EP-A 1 338 533, EP-A 1 388 532, DE-A 102 35 847, WO 98/01415, EP-A 1 015 411, EP-A 1 015 410, WO 99/50219, WO 00/53560, WO 02/09839, DE-A 102 35 847, WO 03/041833, DE-A 102 23 058, DE-A 102 43 625, DE-A 103 36 386, EP-A 854 129, U.S. Pat. No. 4,317,926, DE-A 198 37 520, DE-A 196 06 877, DE-A 195 01 325, DE-A 102 47 240, DE-A 197 40 253, EP-A 695 736, EP-A 1 041 062, EP-A 117 146, DE-A 43 08 087, DE-A 43 35 172, DE-A 44 36 243, DE-A 103 32 758 and DE-A 199 24 533. In principle, however, it is also possible to proceed as described in DE-A 103 36 386, DE-A 101 15 277, DE-A 196 06 877, EP-A 920 408, EP-A 1 068 174, EP-A 1 066 239, EP-A 1 066 240, WO 00/53560, WO 00/53561, DE-A 100 53 086, WO 01/96271, DE-A 10 2004 032 129, WO 04/063138, WO 04/35514, DE-A 102 43 625 and DE-A 102 35 847.

When the hydrocarbon to be dehydrogenated for the process according to the invention is propane, it will preferably be supplied to the reaction gas mixture stream supplied into the reaction zone RZ as a constituent of crude propane in accordance with the teaching of DE-A 102 45 585.

Generally, the reaction gas mixture stream supplied into the reaction zone RZ will comprise hydrocarbon to be dehydrogenated at least to an extent of 5% by volume. Frequently, this proportion by volume will be at values on a corresponding basis of ≥10% by volume, often ≥15% by volume and usually ≥20% by volume or ≥25% by volume, or ≥30% by volume. In general, this proportion by volume, however, will be at values on the same basis of ≤90% by volume, usually ≤80% by volume and often ≤70% by volume. The above data apply especially in the case of propane as the hydrocarbon to be dehydrogenated and propylene as the dehydrogenated hydrocarbon. Of course, they also apply when isobutane is the hydrocarbon to be dehydrogenated and isobutene is the dehydrogenated hydrocarbon.

In addition, the aforementioned reaction gas mixture stream may comprise:
a) $N_2$ and $H_2O$;
b) $N_2$, $O_2$ and $H_2O$;
c) $N_2$, $O_2$, $H_2O$ and $H_2$;
d) $N_2$, $O_2$, $H_2O$, $H_2$ and $CO_2$;
e) $N_2$, $O_2$, $H_2O$, $H_2$, $CO_2$ and CO.

In favorable cases, the reaction gas mixture stream supplied to the reaction zone RZ in the process according to the invention is formed by combining, for example, crude propane, molecular hydrogen and partial oxidation cycle gas. Appropriately from an application point of view, the crude propane and the molecular hydrogen are combined beforehand, and this mixture is heated to reaction temperature (this is typically a temperature of ≥300° C., preferably ≥350° C. and in many cases ≥400° C.). The partial oxidation cycle gas is likewise heated to reaction temperature. Both heating steps can be effected by indirect heat exchange with hot product gas mixture of the process according to the invention. Subsequently, the two preheated gas streams are combined to give the reaction gas mixture stream to be supplied to the reaction zone RZ. An increase in the temperature of the reaction gas mixture stream supplied to the reaction zone RZ which may be required in the context of the inventive long-term operation can be brought about, for example, by intensification of the indirect heat exchange.

Finally, it should be pointed out once again that, for the purpose of the inventive long-term operating mode, the measures of direct and indirect temperature control may each be employed alone or else in combination. The process according to the invention can be implemented in a particularly simple manner in staged reactors whose stages are configured adiabatically, and where the control and flow variations required in each case for dehydrogenation auxiliary gases which are supplied if appropriate can be made between two stages. The number of stages is variable within a wide range. Appropriately from an application point of view, the catalyst stages are charged with dehydrogenation catalyst in an identical manner. Favorably, the number of stages is three, or a whole multiple (for example six, nine, twelve) thereof. Instead of a staged reactor, it is, however, also possible to employ a series connection of a number of adiabatic single reactors corresponding to the number of stages, and to employ the control measures between such reactors. In principle, the inventive procedure can also be applied to a single catalyst bed continuous without interruption in flow direction. Generally, the inventive procedure, in the case of a heterogeneously catalyzed partial dehydrogenation, achieves operating times before a next regeneration of the catalyst bed which are at least 20 hours, but in many cases up to 100 hours and more.

WORKING EXAMPLE AND COMPARATIVE EXAMPLE a) Description of the Dehydrogenation Reactor The dehydrogenation reactor used was a steel tube (stainless steel of DIN materials number 1.4841) of length 2070 mm, of wall thickness 1 mm and of internal diameter 36.4 mm. The tubular reactor was flowed through by the reaction gas mixture stream from the top downward. A 115 mm-high catalyst base made of the same stainless steel projected into the lower end of the tubular reactor, and supported the overall fixed catalyst bed (consisting of three partial fixed catalyst beds of approximately identical bulk density) in a structured manner from the top downward as follows:

790 mm bed length of (inert) steatite spheres (diameter 4-5 mm) of C-220 steatite from CeramTec (internal heating bed);

195 mm bed length of dehydrogenation catalyst (Pt/Sn alloy which had been promoted with the elements Cs, K and La in oxidic form and which had been applied to the outer and inner surface of $ZrO_2 \cdot SiO_2$ mixed oxide support extrudates (mean length (Gaussian distribution in the range from 3 mm to 12 mm with maximum at approx. 6 mm): 6 mm, diameter: 2 mm) in the elemental stoichiometry (mass ratio including support) $Pt_{0.3}Sn_{0.6}La_{3.0}Cs_{0.5}K_{0.2}(ZrO_2)_{88.3}(SiO_2)_{7.1}$ (catalyst precursor preparation and activation to the active catalyst as in example 4 of DE-A 102 19 879);

145 mm bed length of steatite spheres (diameter 4-5 mm) of C-220 steatite from CeramTec;

190 mm bed length of the aforementioned dehydrogenation catalyst;

145 mm bed length of steatite spheres (diameter 4-5 mm) of C-220 steatite from CeramTec;

195 mm bed length of the aforementioned dehydrogenation catalyst;

20 mm bed length of steatite spheres (diameter 1.5-2.5 mm) of C-220 steatite from CeramTec; and 210 mm bed length of steatite spheres (diameter 4-5 mm) of C-220 steatite from CeramTec.

Above the internal heating bed, the steel tube was empty.

The tubular reactor was inserted externally, in the sense of a preheating zone, for the length of the uppermost 400 mm of the heating bed from the top downward (toward the catalyst bed), into two half-shells made of copper (thickness of shell=25 mm) which ensure equal distribution of the amount of heat supplied, which were electrically heated by means of a heating band completely surrounding them. A winding of thermoelectric insulation material was present around the heating band.

From the bottom upward (beginning just below the catalyst base surface), the tubular reactor was inserted for a length of 1530 mm into two pairs of thermally insulating half-shells (thickness of one half-shell=25 mm) made of MPS-Super G from Microtherm in Germany, which were mounted offset by 90° relative to one another. The insulating half-shells were in turn surrounded by a cylindrical shell of stainless steel (external diameter=168 mm, internal diameter=154 mm), around which a radiative oven (length=1600 mm) was arranged for the purpose of trace heating. In this way, the heat flux from the environment into the reaction tube and out of the reaction tube into the environment was minimized along the adiabatic zone.

In addition, a 2500 mm-long thermowell (external diameter=6 mm; internal diameter=4 mm) was introduced into the middle (center) of the reaction tube, into which a multiple thermoelement (a total of 14 measurement points every 8 cm from the lower reactor end upward, thickness 3.2 mm) was introduced.

In addition, two lance pairs have been introduced into the tubular reactor. One pair had been introduced into the tubular reactor from the bottom and the other pair from the top. The lances of one pair were each conducted adjacently between thermowell and internal reactor wall in such a way that they were positioned in the middle between thermowell and internal reactor wall over the tube cross section. Projected into a tubular cross-sectional plane, the two pairs were opposite one another on a tube diameter. The external diameter of a lance manufactured from stainless steel of DIN materials number 1.4841 was 3.17 mm and its internal diameter was 2.17 mm. The length of the lances of one pair was different. Air was metered in through one of the two lances of a lance pair in each case, and reaction gas mixture was withdrawn for analysis purposes through the other lance in each case of a lance pair. The opening of the first analysis lance (LI) in flow direction was placed 20 mm beyond the first partial fixed catalyst bed in flow direction. The opening of the accompanying metering lance (ZI) was placed 100 mm upstream of the second partial fixed catalyst bed in flow direction. The opening of the second analysis lance (LII) was placed 20 mm beyond the second partial fixed catalyst bed in flow direction.

The opening of the accompanying metering lance (ZII) was placed 100 mm upstream of the third partial fixed catalyst bed in flow direction.

Upstream of the tubular reactor, a steel tube of length 1300 mm filled with steatite spheres (of C-220 steatite from CeramTec, diameter 4-5 mm) was inserted as a heater. The reaction gas mixture stream was preheated therein to its entrance temperature into the tubular reactor and simultaneously mixed ideally. For this purpose, the heater tube (stainless steel of DIN materials number 1.4841, wall thickness 3.6 mm, internal diameter 53.1 mm) was heated electrically at a midpoint length of 1200 mm by means of heating collars applied around it from Horst, Heidelberg, Germany. The connection between heater and tubular reactor was accomplished by means of a thermally heated stainless steel tube thermally insulated with customary thermal insulation materials (stainless steel of DIN materials number 1.4841, external diameter 14 mm, internal diameter 10 mm, length 300 mm).

b) Beginning of an Inventive Long-Term Operation (Operating Time $t_0$)

The overall catalyst bed was charged with fresh dehydrogenation catalyst. The reaction gas mixture stream supplied to the overall fixed catalyst bed was a mixture of crude propane, steam and partial oxidation cycle gas of a heterogeneously catalyzed two-stage partial oxidation of the propylene obtained in the dehydrogenation to acrylic acid. The constituents other than propane and propylene were removed from the product gas mixture of the dehydrogenation as described in comparative example 1 of German application 10 2005 013 039 by absorptive/desorptive means (stripping with air). The partial oxidation of propylene to acrylic acid was likewise effected as described in German application 10 2005 013 039. The same applies to the formation of the partial oxidation cycle gas.

As described in German application 10 2005 013 039, the reaction gas mixture stream was obtained in an evaporator with an exit temperature of about 200° C. and supplied starting from there to the heater (the attachment of the evaporator to the heater was configured like that of the heater to the tubular reactor).

The heating of the heater was controlled in such a way that the reaction gas mixture stream passed from the evaporator into the heater left it with a temperature of about 400° C. The reaction gas mixture stream was then conducted into the tubular reactor and heated further in the preheating zone thereof and finally conducted through the tubular reactor. In each case about 30 l (STP)/h of air which had a temperature of 25° C. on entry into the particular lance were metered in via the metering lances ZI and ZII. After an operating time of $t_0$=1 h, the process operation attained its (quasi-)steady operating state essentially for the first time.

The contents of the reaction gas mixture stream supplied to the tubular reactor (all gas composition data in this document are always based on gas chromatography analysis) of 2807 l (STP)/h and the contents of the reaction gas mixture stream when leaving the first, second and third partial fixed catalyst bed were as reported in table 1.

TABLE 1

|  | Reactor inlet | After 1st partial bed | After 2nd partial bed | After 3rd partial bed |
|---|---|---|---|---|
| ppm by vol. of acrolein | 235 | <2 | <2 | <2 |
| ppm by vol. of acrylic acid | 344 | <2 | <2 | <2 |
| ppm by vol. of acetic acid | 170 | <2 | <2 | <2 |
| % by vol. of hydrogen | 0.05 | 2.42 | 3.15 | 4.37 |
| % by vol. of oxygen | 2.93 | <2 | <2 | <2 |
| % by vol. of nitrogen | 53 | 51 | 51 | 51 |
| % by vol. of carbon monoxide | 0.36 | 0.15 | 0.16 | 0.18 |
| % by vol. of carbon dioxide | 1.29 | 2.20 | 2.53 | 2.48 |
| ppm by vol. of methane | 39 | 175 | 342 | 386 |
| ppm by vol. of ethane | 305 | 313 | 357 | 447 |
| ppm by vol. of ethene | 328 | 397 | 565 | 599 |
| ppm by vol. acetylene | 2 | 14 | 25 | 26 |
| % by vol. of propane | 35.4 | 32.5 | 29.6 | 27.8 |
| ppm by vol. of cyclopropane | 200 | 85 | 35 | 19 |
| % by vol. of propene | 0.34 | 4.92 | 6.90 | 7.33 |
| ppm by vol. of propadiene | <2 | <2 | <2 | <2 |
| ppm by vol. of propyne | <2 | 28 | 50 | 52 |
| ppm by vol. of isobutane | 71 | 63 | 57 | 51 |
| ppm by vol. of n-butane | 3 | 3 | 3 | 3 |
| ppm by vol. of trans-butene-2 | 2 | 2 | 2 | 3 |
| ppm by vol. of butene-1 | <2 | <2 | 2 | 3 |
| ppm by vol. of isobutene | 5 | 7 | 12 | 17 |
| ppm by vol. of cis-butene-2 | <2 | <2 | 2 | 2 |
| ppm by vol. of butadiene-1,3 | 7 | 2 | 2 | 2 |
| ppm by vol. of other $C_2$-$C_4$ hydrocarbons | <2 | <2 | <2 | <2 |
| ppm by vol. of benzene | 83 | 69 | 69 | 78 |
| ppm by vol. of total remaining $C_5$ hydrocarbons | 34 | 9 | 10 | 17 |
| ppm by vol. of total remaining $C_6$ hydrocarbons | 8 | 7 | 7 | 5 |

Remaining amount up to 100% by volume = in each case water

As the reaction gas mixture stream passes through the overall catalyst bed, a total of G=(A+B+C) mol % of the molar starting amount KW of hydrocarbon to be dehydrogenated was dehydrogenated therein to dehydrogenated hydrocarbon. A is the contribution of the first partial fixed catalyst bed in flow direction, B is the contribution of the second partial fixed catalyst bed in flow direction and C is the contribution of the third partial fixed catalyst bed in flow direction.

At the operating time $t_0$, the numerical values of G, A, B and C were as follows:

A=12 mol %,
B=5.4 mol %,
C=1.8 mol %, and
G=19.2 mol %,
based in each case on KW.

The temperature $T_1$ of the reaction gas mixture stream in flow direction directly beyond the internal heating bed in the tubular reactor at the operating time $t_0$ was 408° C. The air streams MI and MII metered in via ZI and ZII at the operating time $t_0$ were in each case approx. 33 l (STP)/h.

DESCRIPTION OF THE DRAWINGS c) Performance of an Inventive Long-Term Operation

Figure 2:
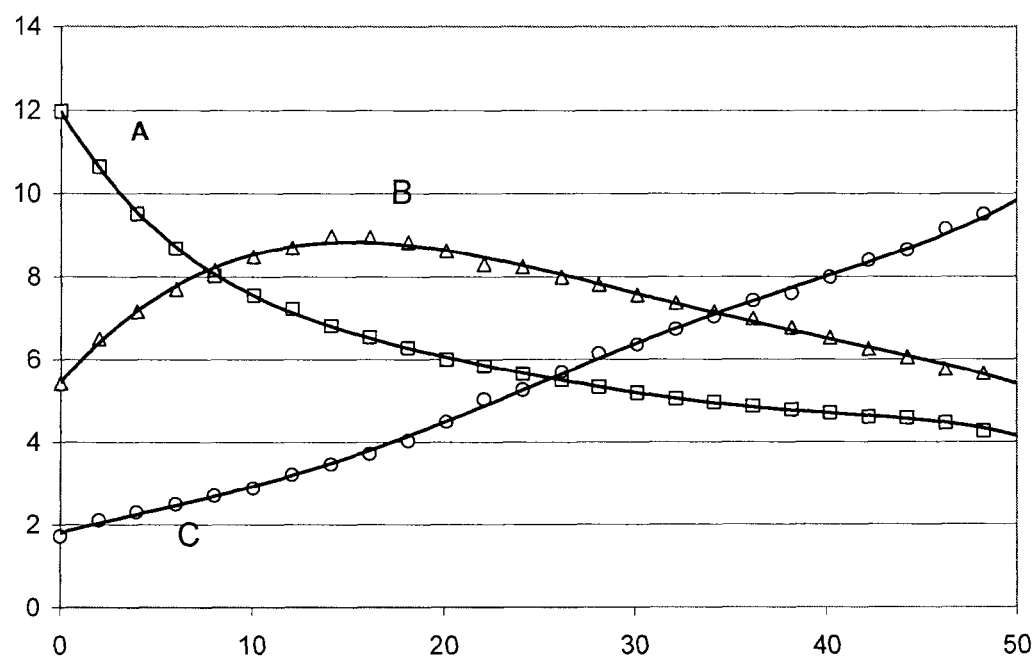
FIG. 2: Resulting profile against time t of the conversion A, B, C proportions

In order to counteract deactivation of the overall fixed catalyst bed which accompanies increasing operating time, both $T_1$ and MI (in FIG. 1=M1) and MII (in FIG. 1=M2) were raised gradually with increasing operating time as shown in FIG. 1 (by the raised data points) (left-hand ordinate=$T_1$ in ° C.; right-hand ordinate=air flow rate in l (STP)/h; the zero point was placed at $t_0$; the abscissa shows t in h). In this manner, it was possible to keep the value for G stable within the interval G=19.2±0.2 mol % over the operating time interval 0 h=$t_0$<t≤50 h. The resulting profile against time (the abscissa shows t in h) of the raised conversion proportions A, B, C (mol % of KW as the ordinate) in the operating time interval is shown by FIG. 2.

Figure 3:
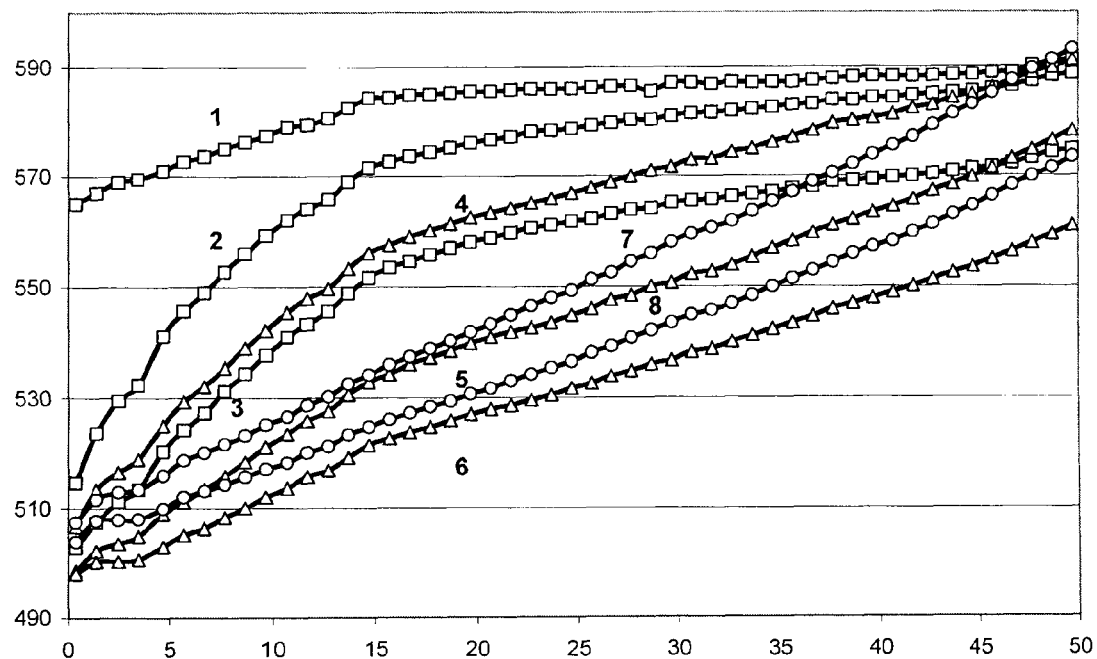
FIG. 3: Profile of the temperature of the reaction gas mixture stream against time The present invention relates to a process for the long-term operation of a continuous heterogeneously catalyzed partial dehydrogenation of a hydrocarbon to be dehydrogenated to a dehydrogenated hydrocarbon, in which, for the purpose of the heterogeneously catalyzed partial dehydrogenation of the hydrocarbon to be dehydrogenated, a reaction gas mixture stream comprising it in a molar starting amount KW is conducted at elevated temperature through an overall catalyst bed which is disposed in a reaction zone RZ and may consist of a plurality of partial catalyst beds arranged in succession in flow direction of the reaction gas mixture stream and comprises in total the amount M of a dehydrogenation catalyst, in such a way that, at the operating time $t=t_0$, a proportion of A mol % of the molar starting amount KW is converted in (single) pass of the reaction gas mixture stream through the first third of the amount M in flow direction, a proportion of B mol % of the molar starting amount KW is converted in (single) pass of the reaction gas mixture stream through the second third of the amount M in flow direction, and a proportion of C mol % of the molar starting amount KW of the hydrocarbon to be dehydrogenated is converted to dehydrogenated hydrocarbon in (single) pass of the reaction gas mixture stream through the last third of the amount M in flow direction, with the proviso that A>B>C, and a total of G=(A+B+C) mol % of the molar starting amount KW of hydrocarbon to be dehydrogenated present therein is dehydrogenated to dehydrogenated hydrocarbon in (single) pass of the reaction gas mixture stream through the overall catalyst bed, and, if appropriate, streams of molecular oxygen, molecular hydrogen, steam and/or other inert gas are supplied as dehydrogenation auxiliary gases to the reaction gas mixture stream between its entry into the start of the overall catalyst bed and its exit from the end of the overall catalyst bed, and the deactivation of the overall catalyst bed which accompanies increasing operating time in an operating time interval of $t_0<t<t_R$, where $t_R$ is the operating time t at which the dehydrogenation is interrupted and the overall catalyst bed is regenerated for the first time after the operating time $t_0$, is counteracted by varying the profile of the temperature of the reaction gas mixture stream within the overall catalyst bed and/or the stream of any dehydrogenation auxiliary gases supplied. The present invention further relates to processes for partial oxidation of the dehydrogenated hydrocarbon obtained.

The resulting profile of the temperature of the reaction gas mixture stream just beyond the inlet (the maximum temperature in the partial bed, reference numeral 1), in the middle (reference numeral 2) and at the outlet (reference numeral 3) of the first partial fixed catalyst bed in flow direction against time is shown (by the raised measurements) in FIG. 3 (the abscissa again shows t in h, the zero point was placed at $t_0$, and the ordinate shows T in ° C.), as is the profile of the temperature of the reaction gas mixture stream just beyond the inlet (the maximum temperature in the partial bed, reference numeral 4), in the middle (reference numeral 5) and at the outlet (reference numeral 6) of the second partial fixed catalyst bed in flow direction and of the third partial fixed catalyst bed in flow direction against time (reference numeral 7=the maximum temperature in the third partial fixed catalyst bed just beyond the inlet into it, reference numeral 8=at the outlet of the third partial fixed catalyst bed).

Subsequently, the process was interrupted, and the overall fixed catalyst bed was regenerated as described in DE-A 100 28 582. Thereafter, the process was restarted. After an operating time of approx. 1 h, the (quasi-)steady operating state had been attained again. Under the original operating conditions, the original value for G was achieved again. The process is operated further in the inventive long-term operation until the next regeneration, etc.

d) Performance of a Noninventive Long-Term Operation

The startup was effected in a manner identical to that described in a), b). In order to counteract the deactivation of the overall fixed catalyst bed accompanying increasing operating time, $T_1$ and the air flow rates MI and MII were each raised with increasing operating time in such a way that the contributions A, B, C to the dehydrogenation conversion, and with them their sum G, remained stable.

After an operating time of 17 h, the value for G within the interval of G=19.2±1 mol % could no longer be maintained on the basis of this long-term operating mode. The process was therefore interrupted, and the overall fixed catalyst bed was regenerated as described in DE-A 100 28 582. Subsequently, the process was restarted. Under the original operating conditions, the original value of G could no longer be achieved.

Example and comparative example can of course also be performed in a completely equivalent manner in a staged fixed bed reactor which has three identical fixed bed stages. The air is then supplied between the 1st/2nd and 2nd/3rd stage in flow direction.

U.S. Provisional Patent Application No. 60/833,776, filed Jul. 28, 2006, is incorporated in the present application by literature reference.

With respect to the abovementioned teachings, numerous modifications to and deviations from the present invention are possible.

It can therefore be assumed that the invention, within the scope of the appended claims, can be performed differently to the manner specifically described herein.

The invention claimed is:

1. A process for the long-term operation of a continuous heterogeneously catalyzed partial dehydrogenation of a hydrocarbon to be dehydrogenated to a dehydrogenated hydrocarbon, in which, for the purpose of the heterogeneously catalyzed partial dehydrogenation of the hydrocarbon to be dehydrogenated, a reaction gas mixture stream comprising the hydrocarbon in a molar starting amount KW is conducted at elevated temperature through an overall catalyst bed which is disposed in a reaction zone RZ and optionally consists of a plurality of partial catalyst beds arranged in succession in flow direction of the reaction gas mixture stream and comprises in total the amount M of a dehydrogenation catalyst, and in which, at the operating time t=$t_0$, a proportion of A mol % of the molar starting amount KW is converted as the reaction gas mixture stream passes through the first third of the amount M in flow direction, a proportion of B mol % of the molar starting amount KW is converted as the reaction gas mixture stream passes through the second third of the amount M in flow direction, and a proportion of C mol % of the molar starting amount KW of the hydrocarbon to be dehydrogenated is converted to dehydrogenated hydrocarbon as the reaction gas mixture stream passes through the last third of the amount M in flow direction, with the proviso that A>B>C, and a total of G=(A+B+C) mol % of the molar starting amount KW of hydrocarbon to be dehydrogenated present therein is dehydrogenated to dehydrogenated hydrocarbon as the reaction gas mixture stream passes through the overall catalyst bed, and, optionally, streams of molecular oxygen, molecular hydrogen, steam and/or other inert gas are supplied as dehydrogenation auxiliary gases to the reaction gas mixture stream between its entry into the start of the overall catalyst bed and its exit from the end of the overall catalyst bed, and the deactivation of the overall catalyst bed which accompanies increasing operating time in an operating time interval of $t_0$<t<$t_R$, where $t_R$ is the operating time t at which the dehydrogenation is interrupted and the overall catalyst bed is regenerated for the first time after the operating time t=$t_0$, is actively counteracted by actively varying the profile of the temperature of the reaction gas mixture stream within the overall catalyst bed and/or the stream of any dehydrogenation auxiliary gases supplied, which comprises performing the variation in such a way that, with increasing operating time t, proportion A decreases, proportion B passes through a maximum and proportion C increases, wherein the overall conversion G=(A+B+C) remains constant within the range G±5 mol %, and wherein within the operating time interval $t_0$<t<$t_R$ a temperature growth rate of a temperature $T_3$ of the reaction gas mixture, on entry thereof into the last third of amount M in flow direction, is constantly above a temperature growth rate of a temperature $T_1$ of the reaction gas mixture, on entry thereof into the first third of the amount M in flow direction, and a temperature growth rate of a temperature $T_2$ of the reaction gas mixture, on entry thereof into the second third of the amount M, is initially above the temperature growth rate of $T_3$ to fall below the temperature growth rate of $T_3$ in further operation and to approximate to the lower growth rate of $T_1$ or wherein within the operating time interval $t_0<t<t_R$ a temperature growth rate of a highest temperature $T_3^*$ of the reaction gas mixture stream, as it flows through the last third of the amount M in flow direction, is constantly above a temperature growth rate of a highest temperature $T_1^*$ of the reaction gas mixture stream, as it flows through the first third of the amount M in flow direction, and a temperature growth rate of a highest temperature $T_2^*$ of the reaction gas mixture stream, as it flows through the second third of the amount M in flow direction, is initially above the temperature growth rate of $T_3^*$ to fall below the temperature growth rate of $T_3^*$ in further operation and to approximate to the lower growth rate of $T_1^*$.

2. The process according to claim 1, wherein the hydrocarbon to be dehydrogenated is a $C_2$- to $C_6$-alkane and the dehydrogenated hydrocarbon is a $C_2$- to $C_6$-alkene.

3. The process according to claim 1, wherein the hydrocarbon to be dehydrogenated is n-propane and the dehydrogenated hydrocarbon is propylene.

4. The process according to any of claims 1 to 3, wherein the reaction gas mixture stream comprising the molar starting amount KW of hydrocarbon to be dehydrogenated additionally comprises steam.

5. The process according to claim 1, wherein the reaction gas mixture stream comprising the molar starting amount KW of hydrocarbon to be dehydrogenated additionally comprises molecular oxygen.

6. The process according to claim 1, wherein the reaction gas mixture stream comprising the molar starting amount KW of hydrocarbon to be dehydrogenated additionally comprises molecular hydrogen.

7. The process according to claim 1, wherein G at the operating time $t_0$ is from 10 to 60 mol %.

8. The process according to claim 1, wherein G at the operating time $t_0$ is from 15 to 40 mol %.

9. The process according to claim 1, wherein G at the operating time $t_0$ is from 15 to 30 mol %.

10. The process according to claim 1, wherein, at the operating time $t=t_0$, based on the overall conversion $G=(A+B+C)$, the partial conversion A is from 45 to 80%, the partial conversion B is from 20 to 40% and the partial conversion C is from 0 to 15%.

11. The process according to claim 1, wherein, at the operating time $t=t_0$, based on the overall conversion $G=(A+B+C)$, the partial conversion A is from 55 to 70%, the partial conversion B is from 20 to 35% and the partial conversion C is from 7 to 13%.

12. The process according to claim 1, wherein, with increasing operating time within the operating time interval of $t_0<t<t_R$, the partial conversion A falls below partial conversion C, so that $C>A$.

13. The process according to claim 1, wherein, with increasing operating time within the operating time interval $t_0<t<t_R$, the sequence of partial conversions A, B, C reverses starting from $A>B>C$ to become $C>B>A$.

14. The process according to claim 1, wherein the value A does not go below 20% of its value at the operating time $t=t_0$ within the operating time interval of $t_0<t<t_R$.

15. The process according to claim 1, wherein the values B, C do not exceed 95% of the value of A at the operating time $t=t_0$ within the operating time interval of $t_0<t<t_R$.

16. The process according to claim 1, wherein the reaction zone RZ is configured as an adiabatic staged reactor with simultaneous supply of streams of a dehydrogenation auxiliary gas comprising molecular oxygen between stages.

17. The process according to claim 1, wherein the reaction zone RZ is designed as a series connection of at least two adiabatic dehydrogenation reactors with simultaneous supply of streams of a dehydrogenation auxiliary gas comprising molecular oxygen between immediately successive adiabatic dehydrogenation reactors in series connection.

18. The process according to claim 1, wherein the overall catalyst bed is a fixed bed.

19. The process according to claim 1, wherein the dehydrogenation catalyst is one which has at least one metal deposited on an oxidic support.

20. The process according to claim 19, wherein the at least one metal is an element from the platinum group.

21. The process according to claim 19, wherein the at least one metal is platinum.

22. The process according to claim 1, wherein a product gas stream comprising dehydrogenated hydrocarbon formed in the reaction zone RZ and hydrocarbon to be dehydrogenated which has not been converted in the reaction zone RZ is withdrawn from the reaction zone RZ, and this product gas stream, as such or after removal of at least a portion of its constituents other than the dehydrogenated hydrocarbon and the hydrocarbon to be dehydrogenated, is used to charge at least one oxidation reactor and the dehydrogenated hydrocarbon present therein is subjected in the reactor to a selective heterogeneously catalyzed partial gas phase oxidation with molecular oxygen to give a partial oxidation product gas mixture comprising the partial oxidation product.

23. The process according to claim 22, wherein the hydrocarbon to be dehydrogenated is propane, the dehydrogenated hydrocarbon is propylene and the partial oxidation product is acrolein, acrylic acid or a mixture thereof.

24. The process according to claim 22, wherein partial oxidation product is subsequently removed from the partial oxidation product gas mixture in a separation zone of the selective heterogeneously catalyzed partial gas phase oxidation, and at least a portion comprising unconverted hydrocarbon to be dehydrogenated of the remaining residual gas comprising unconverted hydrocarbon to be dehydrogenated and molecular oxygen, with or without unconverted dehydrogenated hydrocarbon, is recycled as a partial oxidation cycle gas into the reaction zone RZ.

25. The process according to claim 24, wherein the partial oxidation product is removed from the partial oxidation product gas mixture in the separation zone by conversion to the condensed phase.

26. The process according to claim 25, wherein the partial oxidation product is acrylic acid and the conversion to the condensed phase is effected by absorptive and/or condensative measures.

27. The process according to claim 26, wherein a removal of the acrylic acid from the condensed phase is undertaken using at least one thermal separation process.

28. The process according to claim 27, wherein the at least one thermal separation process comprises a crystallizative removal of acrylic acid from the liquid phase.

29. The process according to claim 28, wherein the crystallizative removal is a suspension crystallization.

30. The process according to claim 27, wherein the removal of the acrylic acid is followed by a process for free-radical polymerization, in which removed acrylic acid is polymerized free-radically to prepare polymers.

31. The process according to claim 27, wherein the removal of the acrylic acid is followed by a process for preparing acrylic esters, in which removed acrylic acid is esterified with an alcohol.

32. The process according to claim 31, wherein the process for preparing an acrylic ester is followed by a process for free-radical polymerization, in which acrylic ester thus prepared is polymerized.

33. The process according to claim 1, wherein at the operating time $t_0$ a temperature $T_1$ of the reaction gas mixture on entry thereof into the first third of the amount M in flow direction is greater than a temperature $T_2$ of the reaction gas mixture on entry thereof into the second third of the amount M, and $T_2$ is greater than a temperature $T_3$ of the reaction gas mixture on entry thereof into the last third of the amount M in flow direction.

34. The process according to claim 1, wherein at the operating time t0 a highest temperature $T_1^*$ of the reaction gas mixture stream as it flows through the first third of the amount M in flow direction is greater than a highest temperature $T_2^*$ of the reaction gas mixture stream as it flows through the second third of the amount M in flow direction, and $T_2^*$ is greater than a highest temperature $T_3^*$ of the reaction gas mixture stream as it flows through the last third of the amount M in flow direction.

* * * * *